US006756449B2

(12) United States Patent
Benz et al.

(10) Patent No.: US 6,756,449 B2
(45) Date of Patent: Jun. 29, 2004

(54) ANB BLOCK COPOLYMERS CONTAINING POLY (VINYL PYRROLIDONE) UNITS, MEDICAL DEVICES, AND METHODS

(75) Inventors: Michael Eric Benz, Ramsey, MN (US); Julie A. Alkatout, Saint Paul, MN (US); SuPing Lyu, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 10/246,806

(22) Filed: Sep. 17, 2002

(65) Prior Publication Data

US 2003/0162905 A1 Aug. 28, 2003

Related U.S. Application Data

(60) Provisional application No. 60/360,725, filed on Feb. 27, 2002.

(51) Int. Cl.[7] .......................... C08L 75/00; A61K 31/79
(52) U.S. Cl. ............................... 525/326.9; 525/326.7; 525/123; 424/78.36; 424/78.24; 424/70.15
(58) Field of Search .......................... 525/326.9, 326.7, 525/123; 424/78.36, 78.24, 70.15

(56) References Cited

U.S. PATENT DOCUMENTS

| | | | |
|---|---|---|---|
| 3,948,783 A | 4/1976 | Szabo et al. | |
| 4,100,309 A | 7/1978 | Micklus et al. | |
| 4,119,094 A | 10/1978 | Micklus et al. | |
| 4,254,239 A | 3/1981 | Straub et al. | |
| 4,350,791 A | * 9/1982 | Straub et al. ............... | 525/123 |
| 4,373,009 A | 2/1983 | Winn | |
| 4,459,317 A | 7/1984 | Lambert | |
| 4,487,808 A | 12/1984 | Lambert | |
| 4,527,293 A | 7/1985 | Eckstein et al. | |
| 4,585,666 A | 4/1986 | Lambert | |
| 4,642,267 A | 2/1987 | Creasy et al. | |
| 4,666,437 A | 5/1987 | Lambert | |
| 4,675,361 A | 6/1987 | Ward, Jr. | |
| 4,842,597 A | 6/1989 | Brook | |
| 4,990,357 A | 2/1991 | Karakelle et al. | |
| 5,061,424 A | 10/1991 | Karimi et al. | |
| 5,077,352 A | 12/1991 | Elton | |
| 5,084,315 A | 1/1992 | Karimi et al. | |
| 5,091,205 A | 2/1992 | Fan | |
| 5,160,790 A | 11/1992 | Elton | |
| 5,179,174 A | 1/1993 | Elton | |
| 5,272,012 A | 12/1993 | Opolski | |
| 5,295,978 A | 3/1994 | Fan et al. | |
| 5,302,385 A | 4/1994 | Khan et al. | |
| 5,331,027 A | 7/1994 | Whitbourne | |
| 5,371,147 A | 12/1994 | Spinelli et al. | |
| 5,558,900 A | 9/1996 | Fan et al. | |
| 5,576,072 A | 11/1996 | Hostettler et al. | |
| 5,589,563 A | 12/1996 | Ward et al. | |
| 5,620,738 A | 4/1997 | Fan et al. | |
| 5,624,617 A | 4/1997 | Sorabella et al. | |
| 5,645,931 A | 7/1997 | Fan et al. | |
| 5,662,960 A | 9/1997 | Hostettler et al. | |
| 5,688,855 A | 11/1997 | Stoy et al. | |
| 5,731,087 A | 3/1998 | Fan et al. | |
| 5,804,318 A | 9/1998 | Pinchuk et al. | |
| 5,997,517 A | 12/1999 | Whitbourne | |
| 6,008,184 A | 12/1999 | Pluyter et al. | |

FOREIGN PATENT DOCUMENTS

| | | |
|---|---|---|
| CA | 2153466 | 3/2001 |
| EP | 032251 A1 | 7/1981 |
| JP | 51091313 | 8/1976 |
| WO | WO 90/01345 A1 | 2/1990 |
| WO | WO 99/19004 A2 A3 | 4/1999 |

OTHER PUBLICATIONS

Adelman, "The reactions of vinyl acetate with aliphatic hydroxy compounds. A new synthesis of vinyl ethers," *J Am Chem Soc.*, 1953; 75:2678–2682.

Uyanik, "Synthesis and characterization of five–block copolymers prepared by vinyl pyrrolidinone and a macro initiator with poly(dimethylsiloxane) and polycaprolactone," *J Appl Polym Sci.*, 1997; 64(10):1961–1969.

Uyanik, "Synthesis and characterization of poly(dimethyl sioloxane) containing poly(vinyl pyrrolidinone) block coplymer," *J Appl Polym Sci.*, 1999; 71(11):1915–1922.

Fan, "Advances in Hydrophilic Lubricity for Medical Applications," *Polymer News*, 1992;17:70–74.

Ikada et al., "Lubricious Polymer Surfaces," Technomic Publishing Company, Inc., Lancaster, PA, 1993 (title page, copyright page, and table of contents only).

Kingshott et al., "Surfaces that Resist Bioadhesion," *Current Opinion in Solid State and Minerals Sceince*, 1999;4:403–412.

Prucker et al., "Photochemical Attachment of Polymer Films to Solid Surfaces via Monolayers of Benzophenone Derivatives," *Journal of the American Chemical Society*, 1999;121:7866–8770.

Takahara, "Block Copolymers and Hydrophilicity," Chapter 7 in *Modern Approaches to Wettability: Theory and Applications*, Malcolm et al., Eds., Plenum Press, New York, NY 1992; pp. 179–212.

* cited by examiner

Primary Examiner—James J. Seidleck
Assistant Examiner—Olga Asinovsky
(74) Attorney, Agent, or Firm—Mueting, Raasch & Gebhardt, P.A.

(57) ABSTRACT

$A_n B$ block copolymers, wherein n is at least two, that include A blocks with poly(vinyl pyrrolidone) units and B blocks with urethane groups, urea groups, imide groups, amide groups, ether groups, ester groups, or combinations thereof, as well as medical devices and methods.

70 Claims, No Drawings

ANB BLOCK COPOLYMERS CONTAINING POLY (VINYL PYRROLIDONE) UNITS, MEDICAL DEVICES, AND METHODS

CROSS REFERENCE TO RELATED APPLICATIONS

This application claims priority to U.S. Provisional Application No. 60/360,725, filed on Feb. 27, 2002, which is incorporated herein by reference in its entirety.

FIELD OF THE INVENTION

This invention relates to polymers containing poly(vinyl pyrrolidone) copolymerized with other polymers such as polyurethanes, etc. Such materials are particularly useful as biomaterials in medical devices.

BACKGROUND OF THE INVENTION

The chemistry of block copolymers is extensive and well developed. They can be used to combine the properties of different polymers in one material. For example, a polymer having hydrophilic properties can form one block and a polymer having hydrophobic properties can form another block. Thus, one material can have combinations of properties that neither constituent polymer possesses alone. This can be of significant utility in the medical device arena.

Polymers used to create medical devices are typically chosen for their bulk properties; however, it is often desirable for the surfaces of such medical devices to possess different properties than that of the bulk polymer. For example, it may be desirable for a polymer surface to have a different level of compatibility with other polymers or tissues, surface energy, etc., than that of the bulk polymer. Thus, block copolymers are desirable materials to investigate for their utility in modifying polymer surfaces for medical device applications.

Block copolymers have been used to modify polyurethane surfaces, which are important biomedical polymers used in implantable devices such as artificial hearts, cardiovascular catheters, pacemaker lead insulation, etc. Such block copolymers have been used to enhance antimicrobial properties, lubricity, barrier properties, anticoagulant properties, and the like. For example, U.S. Pat. No. 4,675,361 (Ward, Jr.) discloses a block copolymer for improved biocompatibility. Also, U.S. Pat. No. 5,302,385 (Khan et al.) discloses a polyurethane-poly(vinyl pyrrolidone) copolymer foam having antimicrobial properties coated on a catheter. The resultant polymer is highly branched or a network polymer without a well-defined or controllable block architecture.

Other block copolymers are needed for modifying the surface properties of medical devices.

SUMMARY OF THE INVENTION

The present invention relates to block copolymers, particularly $A_nB$ block copolymers, wherein n is at least two, and more particularly A-B-A block (triblock) copolymers, that include poly(vinyl pyrrolidone) in the A blocks, and urethane groups, urea groups, amide groups, imide groups, ester groups, ether groups, or combinations thereof (e.g., polyurethanes, polyureas, or polyurethane-ureas) in the B block. This includes methods for making such polymers.

The block copolymers of the present invention are particularly useful as biomaterials in medical devices. Certain preferred embodiments of the block copolymers can also provide a lubricious surface (e.g., a slip coating on a polymeric surface). Lubricous surfaces are desirable for many medical devices, particularly the inner surfaces of lead delivery catheters. Coating conventional materials on the inner surfaces of such catheters can be difficult and expensive, however. The block copolymers of the present invention provide an opportunity to more easily manufacture such devices. Methods involving dip coating followed by solvent removal techniques can be used to apply the block copolymers of the present invention to a substrate. Alternatively, the block copolymers can be coextruded with another thermoplastic polymer to form a layered construction. Extrusion methods can also involve reactive coextrusion.

In one embodiment, the present invention provides a thermoplastic $A_nB$ block copolymer, wherein the A blocks include poly(vinyl pyrrolidone) units and the B block is a long-chain organic connecting unit that includes urethane groups, urea groups, imide groups, amide groups, ether groups, or combinations thereof, wherein n is at least two.

The present invention provides medical devices. One such device includes a surface that includes a thermoplastic $A_nB$ block copolymer, wherein the A block includes poly(vinyl pyrrolidone) units and the B block is a long-chain organic connecting unit that includes urethane groups, urea groups, imide groups, amide groups, ester groups, ether groups, or combinations thereof, wherein n is at least two. The "surface" can be the surface of a coating, for example, of a thermoplastic $A_nB$ block copolymer on another substrate, such as a polymeric material. Alternatively, the "surface" can be the surface of an extruded layer, for example, of a thermoplastic $A_nB$ block copolymer, which can be coextruded with another polymeric material, or formed using reactive coextrusion.

The present invention also provides methods of modifying a surface of a medical device. One method includes: preparing a thermoplastic $A_nB$ block copolymer, wherein the A block includes poly(vinyl pyrrolidone) units and the B block is a long-chain organic connecting unit that includes urethane groups, urea groups, imide groups, amide groups, ether groups, ester groups, or combinations thereof, wherein n is at least two; and applying the $A_nB$ copolymer to the surface of the medical device.

The present invention also provides methods of preparing a thermoplastic $A_nB$ block copolymer. One method includes reacting a substantially monofunctional poly(vinyl pyrrolidone) with a functionalized B-block precursor that includes functional groups reactive with the functional groups of the poly(vinyl pyrrolidone) to form the thermoplastic $A_nB$ block copolymer. In an alternative method, the block copolymer is made in one step using a substantially monofunctional poly(vinyl pyrrolidone) with reactants for the functionalized B-block precursor.

As used herein, the term "organic group" refers to a hydrocarbyl group (aliphatic and/or aromatic) optionally including other atoms (e.g., heteroatoms) or groups (e.g., functional groups) replacing the carbon and/or hydrogen atoms. The term "aliphatic group" means a saturated or unsaturated linear (i.e., straight chain), cyclic, or branched hydrocarbon group. This term is used to encompass alkyl (e.g., $-CH_3$) (or alkylene if within a chain such as $-CH_2-$), alkenyl (or alkenylene if within a chain), and alkynyl (or alkynylene if within a chain) groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group"

means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "aromatic group" or "aryl group" means a mono- or polynuclear aromatic hydrocarbon group. These hydrocarbon groups may be substituted with heteroatoms, which can be in the form of functional groups. The term "heteroatom" means an element other than carbon (e.g., nitrogen, oxygen, sulfur, chlorine, etc.).

As used herein, the terms "a," "an," "one or more," and "at least one" are used interchangeably.

As used herein, a "thermoplastic" polymer is one that will melt and flow when heated and reform substantially the same material upon cooling.

As used herein, a "biomaterial" or "biocompatible material" may be defined as a material that is substantially insoluble in body fluids and tissues and that is designed and constructed to be placed in or onto the body or to contact fluid or tissue of the body. Ideally, a biocompatible material will not induce undesirable reactions in the body such as blood clotting, tissue death, tumor formation, allergic reaction, foreign body reaction (rejection) or inflammatory reaction; will have the physical properties such as strength, elasticity, permeability, and flexibility required to function for the intended purpose; can be purified, fabricated, and sterilized easily; and will substantially maintain its physical properties and function during the time that it remains implanted in or in contact with the body.

As used herein, a "medical device" may be defined as an article that has surfaces that contact blood or other bodily tissues in the course of their operation. This can include, for example, extracorporeal devices for use in surgery such as blood oxygenators, blood pumps, blood sensors, tubing used to carry blood, and the like, which contact blood, which is then returned to the patient. This can also include implantable devices such as vascular grafts, stents, electrical stimulation leads, heart valves, orthopedic devices, catheters, guide wires, shunts, sensors, replacement devices for nucleus pulposus, cochlear or middle ear implants, intraocular lenses, and the like.

DETAILED DESCRIPTION OF ILLUSTRATIVE EMBODIMENTS OF THE INVENTION

The present invention provides polymers, medical devices that include such polymers (preferably, biomaterials), and methods of making and using such polymers. Such polymers are suitable for modifying the surface of a substrate, such as in or on a medical device. Such substrates include, for example, polymers such as polyurethanes, polyureas, poly(urethane-urea)s, polyamides, poly(amide-ether)s, polyimides, copolymers or mixtures thereof.

One medical device of particular interest is a catheter such as a lead delivery catheter. Preferably, the inner lumen of the catheter is coated with a polymer of the present invention.

The polymers are preferably $A_nB$ block copolymers, wherein n is at least two, and more preferably A-B-A block copolymers. Each "block" or segment may be a homopolymer, or a random or block copolymer itself. For example, the A block can include one or more poly(vinyl pyrrolidone) (PVP) units, optionally polymerized with other monomers. The B block can include urethane groups, urea groups, amide groups, imide groups, ester groups, ether groups, or combinations thereof. The B block preferably includes urethane groups, urea groups, amide groups, imide groups, ether groups, or combinations thereof. More preferably, the B block includes urethane groups and/or urea groups. Most preferably, the B block includes urethane groups.

Typically, the $A_nB$ block copolymers are prepared from precursor polymers (i.e., prepolymers), although other methods can be used to build polymers with the same block architecture. In a particularly preferred embodiment, the B block is formed from an isocyanate functional prepolymer (e.g., a diisocyanate polyurethane (OCN-PU-NCO)) and the A block is formed from a substantially monofunctional hydroxyl terminated poly(vinyl pyrrolidone) prepolymer (PVP-OH). In this $A_nB$ formulation, the B block is defined to include the functionality formed upon reaction of the A and B prepolymers (e.g., PVP-OH and OCN-PU-NCO prepolymers).

In an exemplary schematic, a preferred $A_nB$ block copolymer is an A-B-A block copolymer, which can be formed according to the following scheme (Scheme I):

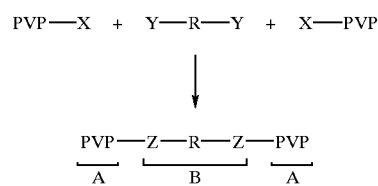

wherein:
X and Y contain at least one reactive functionality selected from the group consisting of primary or secondary amine groups, primary or secondary amides, carboxylic acid groups, hydroxyl groups (e.g., phenols), isocyanate groups, wherein X and Y are selected to be reactive with each other;
Z contains urethane groups, urea groups (e.g., acyl ureas), amide groups, imide groups, ester groups, ether groups, or combinations thereof;
R is a long chain organic (connecting) group; and
PVP-X is a polymer formed from N-vinyl pyrrolidone and other optional monomers.

Each of the individual A and B blocks, as well as the resultant polymer, may be linear or branched, although not so significantly branched that the resultant polymer is not thermoplastic. Preferably, the A and B blocks are both linear, as is the resultant polymer. Because the B block can be branched, it is envisioned that the $A_nB$ block copolymer could be a star block copolymer, for example, wherein n is at least three.

Preferably, the block copolymer of the present invention has a weight average molecular weight of at least about 1000 grams per mole (g/mol), more preferably, at least about 10,000 g/mol in the uncrosslinked state, and most preferably, at least about 20,000 g/mol. Preferably, the block copolymer of the present invention has a weight average molecular weight of no greater than about $3\times10^6$ g/mol in the uncrosslinked state. The molecular weights of the block copolymers can be controlled by well-known synthetic techniques. Typically, for preferred embodiments, the molecular weights of the prepolymers control the final molecular weights of the block copolymers.

If desired, the block copolymer can be crosslinked after application to a surface, particularly a surface of a medical device. Crosslinking can be accomplished using a variety of well-known techniques. This can include the use of electron beam (E-beam). Alternatively, it can be accomplished through the incorporation of unsaturation in the B-block and the use of chemical crosslinkers such as butanediol divinyl ether or divinyl benzene.

If desired, the block copolymer can be mixed with a secondary polymer for various effects. It is particularly desirable to use a constituent polymer of the substrate on which this block copolymer is coated as the secondary polymer to enhance adhesion to the substrate. Examples of suitable secondary polymers include a polyurethane, a polyurea, a poly(urethane-urea), a polyamide, a poly(amide-ether), a polyimide, copolymers or mixtures thereof. Alternatively, poly(vinyl pyrrolidone) can be used as the secondary polymer to further modify the surface properties of the substrate polymer.

Preferably, the block copolymer is lubricious (e.g., slippery). This can be evaluated qualitatively by finger touch. Alternatively, the coefficient of friction (COF) can be determined on wet surfaces as described in the Examples Section. Preferably, a lubricious coating has a COF at least 50% less than, and more preferably, at least 80% less than, that of the uncoated substrate. Alternatively stated, more preferably, the COF of a substrate having a lubricious coating thereon is 20% of the COF of the uncoated substrate or less.

Preferred A Blocks

The A blocks of the $A_nB$ block copolymers wherein n is at least two, preferably A-B-A block copolymers, of the present invention include poly(vinyl pyrrolidone) (PVP). PVP is particularly desirable because PVP homopolymers of at least about 400,000 g/mol (weight average molecular weight) are generally lubricious and biocompatible. Surprisingly, however, lower molecular weight PVP-containing blocks can also provide suitable lubricity. Preferably, the PVP used to form the A blocks has a weight average molecular weight of at least about 1000 g/mol, and more preferably at least about 1500 g/mol. Preferably, the PVP used to form the A blocks has a weight average molecular weight of no greater than about $1 \times 10^6$ g/mol, more preferably, no greater than about 500,000 g/mol, even more preferably, no greater than about 400,000 g/mol, and most preferably, no greater than about 200,000 g/mol.

If desired, the A blocks of the $A_nB$ block copolymers of the present invention could include copolymers of N-vinyl pyrrolidone (i.e., 1-vinyl-2-pyrrolidone) and monomers nonreactive with isocyanate groups or other reactive functional groups on the B-block prepolymer (Y in Scheme I above). Such monomers are selected from the group consisting of (meth)acrylic esters (i.e., acrylic esters and methacrylic esters, also referred to as (meth)acrylates), (meth)acrylamides (i.e., acrylamides and methacrylamides), butadiene, ethylene, alpha-olefins, halogenated olefins (e.g., tetrafluoroethylene), acrylonitrile, isoprene, styrene, vinyl chloride, vinyl fluoride, vinyl esters, vinylidene chloride, N-vinyl carbazole, and combinations thereof. Thus, as used herein a "PVP" prepolymer or "PVP" block is defined as one that includes a polymer of N-vinyl pyrrolidone or copolymers thereof with one or more other monomers. Preferably, a PVP prepolymer or PVP block includes only poly(vinyl pyrrolidone).

The A blocks of the $A_nB$ block copolymers of the present invention are preferably formed from a substantially monofunctional PVP prepolymer. By this it is meant that the PVP prepolymer starting material could have small amounts of difunctional PVP or nonfunctional PVP, although it is primarily monofunctional PVP.

Preferably, the functionalized PVP prepolymer is hydroxyl terminated. Although substantially monofunctional hydroxyl terminated PVP is preferred, other functionalized PVPs could be used to form the A blocks of the $A_nB$ block copolymers of the present invention (e.g., could be any of the X groups in Scheme I above). Preferably, PVP prepolymers (which can be homopolymers or copolymers) could be functionalized with primary or secondary amine groups, carboxylic acid groups, as well as hydroxyls (e.g., phenols), and combinations thereof. More preferably, PVP prepolymers are functionalized with hydroxyl. It should be understood that the PVP-X prepolymers can include other functionality in the X moiety, particularly ether functionality (e.g., —X can be —C(CH$_3$)$_2$—O—CH$_2$C(O)OH or —C(CH$_3$)$_2$—O—CH$_2$CH$_2$OH).

The A blocks can be linear or branched. Preferably, they are linear. A branched A block, for example, could be prepared from a PVP-OH prepolymer reacted with citric acid to form the corresponding triester according to the following schematic (Scheme II):

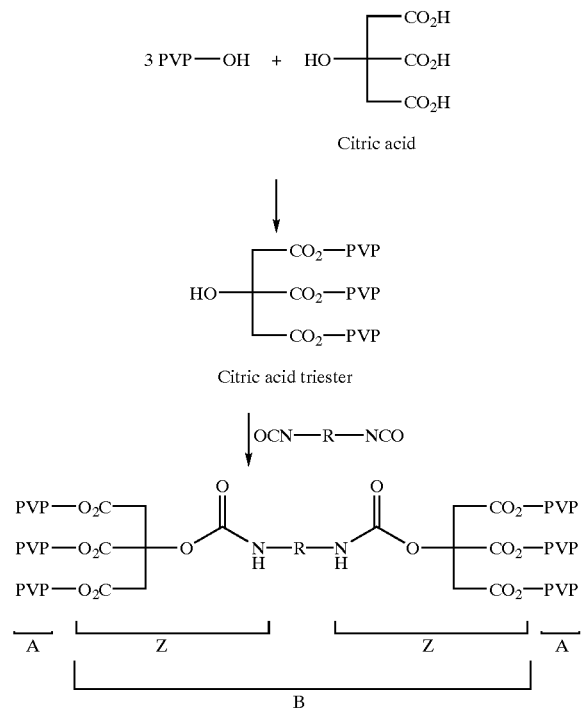

Preferred B Block

The B block of the $A_nB$ block copolymers wherein n is at least two, preferably the A-B-A block copolymers, is a long-chain organic connecting unit between the A blocks. The B block is typically designed to be compatible with, and to adhere to, a particular surface. For example, the B block can be designed to penetrate an underlying polymeric surface and through physical entanglement improve adhesion of the block copolymer.

Typically, the B block is functionalized with urethane groups, urea groups, amide groups, imide groups, ester groups, ether groups, or combinations thereof. Preferably, the B blocks include urethane groups, urea groups (e.g., acyl urea groups), amide groups, imide groups, ether groups, or combinations thereof. More preferably, the B blocks include urethane groups and/or urea groups. Most preferably, the B blocks include urethane groups. The B blocks can optionally include tertiary amine groups, siloxane groups, silane groups, ortho-ester groups, phosphoester groups, thioether groups, sulfoxide groups, sulfone groups, ketone groups, acetal groups, ketal groups, hemiacetal groups, hemiketal groups, epoxy groups, and combinations thereof.

As used herein, "long-chain" refers to an organic connecting unit (i.e., connecting the A blocks) containing 20 atoms or more (preferably, 20 carbon atoms or more). Preferably, a B block includes about 100 atoms or more, more preferably about 500 atoms or more, and most preferably about 1000 atoms or more, connecting the A blocks. Preferably, there are no more than about $1 \times 10^6$ atoms in the chain.

Preferably, the precursor (which is preferably a prepolymer) used to form the B block is functionalized with at least two reactive groups, and more preferably only two reactive groups, which are preferably isocyanate groups. Preferred materials are substantially polyfunctional (i.e., functionalized with groups reactive with the PVP prepolymer). More preferred materials are substantially difunctional. That is, "substantially" polyfunctional or difunctional means that there may be small amounts of monofunctional or nonfunctional prepolymers present in the precursor.

Although isocyanate functionality is preferred, other functionalized precursors could be used to form the B blocks of the $A_nB$ block copolymers of the present invention (i.e., could be any of the Y groups in Scheme I above). Preferably, they could be functionalized with carboxylic acids, hydroxyl groups, primary or secondary amides, as well as isocyanates. More preferably, the B block precursors are functionalized with isocyanates.

Upon reacting such functionalized precursors with functionalized PVP prepolymers, the resultant $A_nB$ block copolymer would result in linking groups (the Z functionality in Scheme I, which are incorporated into the B blocks according to the present invention) that include, for example, urethane groups, urea groups (e.g., acyl ureas), amide groups, imide groups, ester groups, ether groups, or combinations thereof. Preferably, Z includes urethane groups, urea groups, amide groups, imide groups, ether groups, or combinations thereof. More preferably, Z includes urethane and/or urea groups, and most preferably, urethane groups.

The precursors suitable for forming the B blocks of the $A_nB$ block copolymers according to the present invention are preferably diisocyanate terminated prepolymers. They are preferably, diisocyanated terminated polyurethanes, polyureas, or poly(urethane-ureas), and more preferably, diisocyanate terminated polyurethanes. These polymers can vary from hard and rigid to soft and flexible.

The preferred polymers used to form the B blocks of the $A_nB$ block copolymers of the present invention can be homopolymers or copolymers, although preferably, they are random, block, or segmented copolymers (i.e., containing both hard and soft domains or segments).

Such polymers used to form the B blocks can be prepared using a variety of techniques from polymerizable compounds (e.g., monomers, oligomers, or polymers). Such compounds include diols, diamines, or combinations thereof, for example.

Although certain preferred polymers are described herein, the polymers used to form the B blocks of the $A_nB$ block copolymers of the preferred biomaterials in the medical devices of the present invention can be a wide variety of polymers that include urethane groups, urea groups, or combinations thereof. Such polymers are prepared from isocyanate-containing compounds, such as polyisocyanates (preferably diisocyanates), and compounds having at least two hydrogen atoms reactive with the isocyanate groups, such as polyols and/or polyamines (preferably diols and/or diamines).

Typically, the preferred urethane- and/or urea-containing polymers used to form the B block are made using polyisocyanates and polyols and/or polyamides, including polyester, polyether, and polycarbonate polyols, for example, although such polyols are less preferred because they produce less biostable materials. The polyols and polyamines can be aliphatic, cycloaliphatic, aromatic, heterocyclic, or combinations thereof.

Examples of suitable diols for preparing the B-block prepolymers include those commercially available under the trade designation POLYMEG and other polyethers such as polyethylene glycol and polypropylene oxide, polybutadiene diol, dimer diol (e.g., that commercially available under the trade designation DIMEROL (from Uniqema, New Castle, Del.)), polyester-based diols such as those commercially available under the trade designations STEPANPOL (from Stepan Corp., Northfield, Ill.), CAPA (a polycaprolactone diol from Solvay, Warrington, Cheshire, United Kingdom), and TERATE (from Kosa, Houston, Tex.), poly (ethylene adipate) diol, poly(ethylene succinate) diol, poly (1,4-butanediol adipate) diol, poly(caprolactone) diol, poly (hexamethylene phthalate) diol, and poly(1,6-hexamethylene adipate) diol, as well as polycarbonate-based diols such as poly(hexamethylene carbonate) diol.

Other polyols can be used as chain extenders to form the B block precursors, as is conventionally done in the preparation of polyurethanes, for example. Examples of suitable chain extenders include 1,10-decanediol, 1,12-dodecanediol, 9-hydroxymethyl octadecanol, cyclohexane-1,4-diol, cyclohexane-1,4-bis(methanol), cyclohexane-1,2-bis(methanol), ethylene glycol, diethylene glycol, 1,3-propylene glycol, dipropylene glycol, 1,2-propylene glycol, trimethylene glycol, 1,2-butylene glycol, 1,3-butanediol, 2,3-butanediol, 1,4-butanediol, 1,5-pentanediol, 1,6-hexanediol, 1,2-hexylene glycol, 1,2-cyclohexanediol, 2-butene-1,4-diol, 1,4-cyclohexanedimethanol, 2,4-dimethyl-2,4-pentanediol, 2-methyl-2,4-pentanediol, 1,2,4-butanetriol, 2-ethyl-2-(hydroxymethyl)-1,3-propanediol, glycerol, 2-(hydroxymethyl)-1,3-propanediol, neopentyl glycol, pentaerythritol, and the like.

Examples of suitable polyamines (typically diamines) for making the B-block prepolymers include ethylenediamine, 1,4-diaminobutane, 1,10-diaminodecane, 1,12-diaminododecane, 1,8-diaminooctane, 1,2-diaminopropane, 1,3-diaminopropane, tris(2-aminoethyl)amine, lysine ethyl ester, and the like.

Examples of suitable mixed alcohols/amines for making the B-block prepolymers include 5-amino-1-pentanol, 6-amino-1-hexanol, 4-amino-1-butanol, 4-aminophenethyl alcohol, ethanolamine, and the like.

Suitable isocyanate-containing compounds for preparation of polyurethanes, polyureas, or poly(urethanes-ureas), are typically aliphatic, cycloaliphatic, aromatic, and heterocyclic (or combinations thereof) polyisocyanates. In addition to the isocyanate groups they can include other functional groups such as biuret, urea, allophanate, uretidine dione (i.e., isocyanate dimer), and isocyanurate, etc., that are typically used in biomaterials. Suitable examples of polyisocyanates include 4,4'-diisocyanatodiphenyl methane (MDI), 4,4'-diisocyanatodicyclohexyl methane (HMDI), cyclohexane-1,4-diisocyanate, cyclohexane-1,2-diisocyanate, isophorone diisocyanate, tolylene diisocyanates, naphthylene diisocyanates, benzene-1,4-diisocyanate, xylene diisocyanates, trans-1,4-cyclohexylene diisocyanate, 1,4-diisocyanatobutane, 1,12-diisocyanatododecane, 1,6-diisocyanatohexane, 1,5-diisocyanato-2-methylpentane, 4,4'-methylenebis (cyclohexyl isocyanate), 4,4'-methylenebis(2,6-diethyphenyl isocyanate), 4,4'-methylenebis(phenyl isocyanate), 1,3-phenylene diisocyanate, poly((phenyl isocyanate)-co-formaldehyde), tolylene-2,4-diisocyanate, tolylene-2,6-diisocyanate, dimer diisocyanate, as well as polyisocyanates available under the trade designations DESMODUR RC, DESMODUR RE, DESMODUR RFE, and DESMODUR RN from Bayer, and the like.

The relatively hard segments of the polymers of the present invention (typically present in the B blocks) are preferably fabricated from short to medium chain diisocyanates and short to medium chain diols or diamines, all of which preferably have molecular weights of less than about 1000. Appropriate short to medium chain diols, diamines, and diisocyanates include straight chain, branched, and cyclic aliphatics, although aromatics can also be used. Examples of diols and diamines useful in these more rigid segments include both the short and medium chain diols or diamines discussed above.

Methods of Preparing the Block Copolymers

The $A_nB$ block copolymers of the present invention can be made by a variety of methods involving condensation polymerization such as metathesis polymerization or reaction of complementary functional groups.

Preferably, the method includes reacting a substantially monofunctional poly(vinyl pyrrolidone) with a functionalized B-block precursor comprising functional groups reactive with the functional groups of the poly(vinyl pyrrolidone). Preferably, the substantially monofunctional poly(vinyl pyrrolidone) is hydroxyl terminated. Preferably, this is prepared by polymerizing N-vinyl pyrrolidone in the presence of a hydroxyl terminated chain transfer agent, such as isopropoxyethanol. Preferably, the functionalized B-block precursor is a diisocyanate terminated prepolymer that includes urethane groups, urea groups, amide groups, imide groups, ether groups, or combinations thereof, and more preferably urethane and/or urea groups.

The PVP (prepolymer) precursors, whether homopolymers or copolymers (which include two or more monomers), can be made using standard techniques such as radical polymerication. They can be functionalized using radical polymerization in the presence of a functionalized chain transfer agent. Examples of suitable functional groups include carboxylic acid, amine, amide, and silane groups. Typical functionalized chain transfer agents and reaction conditions are disclosed in the Examples Section below.

The B-block (prepolymer) precursor can be made using standard techniques. For example, B-block prepolymers can be made using condensation polymerization, ring-opening metathesis polymerization, and radical polymerization. For example, B-block urethane-containing prepolymers can be made using standard polyurethane synthesis techniques. Typical conditions are disclosed in the Examples Section below.

Preferred conditions for forming the $A_nB$ block copoloymers include the use of an inert atmosphere (e.g., nitrogen or argon), temperatures of about 20° C. to about 150° C. (more preferably, about 50° C. to about 100° C.), reaction times of about 1 hour to about 3 days (more preferably, about 1 hour to about 24 hours). The A- and B-block (prepolymer) precursors are typically combined under such conditions to form the $A_nB$ block copolymers of the present invention.

Alternatively, the $A_nB$ block copolymers of the present invention can be made in one step. Typically, this involves combining the reactants for making the B-block precursor with the A-block precursor. This is exemplified in Example 14.

In addition to the $A_nB$ block copolymers described herein, biomaterials of the invention can also include a variety of additives. These include antioxidants, colorants, processing lubricants, stabilizers, imaging enhancers, fillers, and the like.

Methods of Modifying a Surface

The block copolymers of the present invention are preferably used to modify a surface of a medical device. This includes preparing an $A_nB$ block copolymer and (subsequently or simultaneously) applying it to the surface of the medical device in any of a wide variety of manners.

For example, the block copolymer can be applied to a surface out of a solution. This can be done, for example, by dip coating, roll coating, spraying, inkjet printing, or combinations thereof.

Suitable solvents for solution coating include, for example, dimethyl formamide, dimethyl sulfoxide, tetrahydrofuran, chloroform, water, isopropanol, ethanol, acetone, acetonitrile, dioxane, dimethyl acetamide, N-methyl pyrrolidone, or combinations thereof. Preferred solvents for solution coating include, for example, dimethyl formamide, dimethyl sulfoxide, tetrahydrofuran, dimethyl acetamide, N-methyl pyrrolidone, water, or combinations thereof.

The polymer content of a coating solution depends in part on the desired coating weight. Typically, the polymer content of a coating solution is at least about 0.1 percent by weight (wt-%), and preferably at least about 1.0 wt-%, based on the total weight of the solution. Typically, the polymer content of a coating solution is no more than about 40 wt-%, and preferably no more than about 20 wt-%, based on the total weight of the solution.

The temperature for coating is preferably about 25° C., but can be as low as about 0° C. and as high as the melting point of the polymer or the boiling point of the solvent (whichever is lower). The time period for coating can be as short as 0.1 second (e.g., dipping), but not so long as would result in dissolution of the substrate polymer. Typically, no more than about 5 minutes is required.

The coated sample can be subjected to elevated temperatures. Typically, any temperature above room temperature but below the melting point of either the substrate polymer or the block copolymer of the present invention. A typical temperature is at least about 70° C. The exposure time at this elevated temperature is sufficient to remove the solvent and promote adhesion of the block copolymer of the present invention to the substrate polymer. A typical time is at least about 18 hours. Simultaneously or subsequently, the coated sample could be subjected to reduced pressure (e.g., a vacuum) to enhance solvent removal.

In other embodiments, the block copolymer can be applied to a surface by coextruding the block copolymer with a substrate polymer. In a typical coextrusion process, two or more polymers are simultaneously extruded by two or more extruders into a common die. These polymers are combined at the extruder head to produce a multilayer structure. For example, if it is desired to make a catheter, a tube could be produced that has a sandwich structure comprising the different polymers used in the coextrusion.

Coextrusion permits the properties of the various polymers used in the coextrusion process to be combined. For example, coextruding a polymer with acceptable strength properties and a polymer with acceptable environmental resistance may create an article with both strength and environmental resistance. The multilayer structure created using coextrusion has the strong polymer sandwiched between layers of the polymer with environmental resistance, thus permiting the creation of the article with the desired combination of properties. Coextrusion has certain advantages over other methods of combining properties, including cost effectiveness and the ability to alter the properties of the surface of the inner lumen of small diameter tubing.

For successful co-extrusion, it is desirable for the polymers to have compatible properties. This compatibility permits good adhesion between the coextruded layers and ensures the integrity of the extruded article. One way of obtaining this compatibility is for the polymers to be coextruded to share at least one common block. For example, a polyurethane tube with different properties on the surface of the inner lumen may be created by coextruding the polyurethane with a copolymer comprising polyurethane blocks and blocks with the desired surface properties.

Coextrusion conditions, e.g., temperature, pressure, flow rates, will vary depending on the polymers and can be determined by one of skill in the art without undue experimentation. For guidance see the Examples Section below.

Coextrusion can also involve reactive coextrusion of one or more layers (e.g., substrate polymer layer lubricious coating layer). This typically involves combining prepolymers (e.g., A- and B-block prepolymers) in the extruder under conditions effective to cause reaction thereof. Alternatively, reactants for forming the prepolymers can be combined in the extruder.

Reactive coextrusion can result in the in situ formation of block or grafted copolymers or crosslinked copolymer structures at the interface between the coextruded layers. This provides entanglement between the two layers and enhanced adhesion. As above, reactive coextrusion conditions will vary depending on the polymers and can be determined by one of skill in the art without undue experimentation. For guidance see the Examples Section below.

Layers of $A_nB$ copolymers of the present invention can be as thick as needed for the intended purpose. Desirably, as thin a layer as possible is used to provide the intended properties (e.g., lubricity). For example, coatings as thin as 1 micron and as thick as 0.4 mm have been prepared with slippery properties.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXAMPLES

Example 1

Synthesis of Hydroxyl-Terminated Poly(N-vinyl-pyrrolidone)

MATERIALS: The monomer N-vinyl-pyrrolidone was purchased from Aldrich Chemical Co., Milwaukee, Wis., and the NaOH inhibitor was removed by vacuum distillation. The monomer was stored in a freezer prior to use. All other reagents were used as received from Aldrich Chemical Co., including: anhydrous diethyl ether, 2,2-azobisisobutyronitrile (AIBN), and the chain transfer agent 2-isopropoxyethanol.

SYNTHESIS: In an oven-dried, nitrogen-purged, 1000-mL, 3-neck round-bottomed flask equipped with a magnetic stir bar, thermocouple, oil bubbler, and heating mantle, 5.2 grams (g) N-vinyl-pyrrolidone and 0.5 g AIBN were dissolved into 451.5 g (500 milliliters (mL)) isopropoxyethanol chain transfer agent. Nitrogen gas was bubbled through the reaction solution for about 30 minutes with stirring, prior to activating the AIBN with heat. The reaction mixture was slowly heated to 80° C. Upon heating, the nitrogen sparge tube was pulled out of the solution to purge the overhead space for the duration of the reaction. The reaction mixture was heated for 24 hours. The solution was then transferred to a single-neck, 1000-mL, round-bottomed flask for roto-evaporation. Isopropoxyethanol (300 mL) was used to rinse the solution out of the reaction vessel. The isopropoxyethanol was evaporated at 50° C. and 18 mm Hg (2.4 kPa) until the total volume remaining was approximately 25 mL. This concentrated solution was poured into a Waring blender containing cold ether. With fast stirring, a white precipitate formed and was collected by filtration using a Buchner funnel. The product was a white powder and 1.62 g were obtained, corresponding to a 31% yield. The low yield was due to multiple precipitation attempts before a successful procedure was established. The white powder was purified in a Soxhlet extraction set up containing 500 mL ether. The extraction was run for 24 hours. The product was dried under vacuum at 50° C. for three days to remove the ether.

The molecular weight data obtained by GPC was as follows: number average molecular weight (MN)=5570 g/mol, weight average molecular weight (MW)=9420 g/mol, polydispersity (PDI)=1.69. The hydroxyl functionality was confirmed by reacting the PVP-OH with an isocyanate-terminated prepolymer, synthesized as in Example 2, made of diisocyanatodiphenyl methane (MDI) and poly(tetra-methylene oxide) (PTMO). The isocyanate peak at 2270 $cm^{-1}$ that was present in the prepolymer IR spectrum disappeared upon the addition of the PVP-OH.

New peaks corresponding with urethane linkages at 3266 $cm^{-1}$ and 1727 $cm.^{-1}$ were present in the IR spectrum of the product. This data supports that the poly(vinyl pyrrolidone) was hydroxyl-terminated.

Example 2

Synthesis of Isocyanate-Teminated B-block Prepolymer

MATERIALS: QO POLYMEG 1000 (PTMO), which is a poly(tetra-methylene oxide), was purchased from Penn Specialty Chemicals, Inc., Memphis, Tenn. The PTMO was dried under full vacuum at 100° C. Flaked MONDUR M (MDI) was purchased from Bayer Corporation, Rosemount, Ill. and stored in a freezer until use. Anhydrous dioxane was purchased from Aldrich and was used as received.

SYNTHESIS: Inside a nitrogen-atmosphere glove box, 15.71 g (15.43 mmol) PTMO and 80 g anhydrous dioxane were added to a 3-neck 250-mL round-bottomed flask equipped with magnetic stir bar, thermocouple and air condenser for gas expansion. The solution was stirred and allowed to equilibrate at 73° C. before 4.32 g (17.21 mmol) MDI was added to the reaction vessel. The reaction mixture was heated up to 93° C. briefly and the remainder of the reaction was run at 74° C. The reaction was run overnight and the viscosity was noticeably higher the next morning.

The reaction was monitored by IR spectroscopy. The NCO peak at 2270 $cm^{-1}$ was initially very strong and there was a broad absorption around 3500 $cm^{-1}$, corresponding to the PTMO hydroxyl groups. Eighteen hours later, the absorption around 3500 $cm^{-1}$ was gone and a new broad peak around 3300 $cm^{-1}$ formed, indicating urethane bond formation. A small isocyanate peak at 2270 cm$^{-1}$ remained, indicating the prepolymer was isocyanate-terminated. The isocyanate groups of the prepolymer were quenched with ethanol prior to GPC analysis. The molecular weight results by GPC were: MN=40,800 g/mol, MW=69,500 g/mol, PDI=1.71.

Example 3

Synthesis of a PVP-Polyurethane-PVP Block Copolymer

MATERIALS: Hydroxyl-terminated poly(N-vinyl pyrrolidone) (PVP-OH) was synthesized as described in Example 1. Prior to this reaction the PVP-OH was dried under full vacuum at 50° C. for two days. The isocayanate-terminated B-block prepolymer was synthesized as described in Example 2. Anhydrous dioxane and anhydrous dimethylacetamide (DMAC) were purchased and used as received.

SYNTHESIS: Inside a nitrogen atmosphere glove box, 0.4 g PVP-OH was dissolved in 1.62 g anhydrous DMAC in a dry 20-mL screw-top reaction tube. Next, 2.16 g of a 20% solution of the isocyanate-terminated B-block prepolymer in dioxane was added to the reaction vessel. The reaction mixture was shaken and placed in a 60° C. oven inside the nitrogen glove box for eighteen hours. The reaction was monitored by IR spectroscopy. The isocyanate peak at 2270 cm$^{-1}$ that was present in the prepolymer spectrum disappeared upon the addition of the PVP-OH. New peaks corresponding with urethane linkages at 3266 cm$^{-1}$ and 1727 cm$^{-1}$ were present in the spectrum of the product. The solvents were removed by roto-evaporation. The total yield of PVP-PU-PVP triblock copolymer was 0.52 g, corresponding to a 65% yield.

The following summarizes the spectral properties observed by IR: 3266, 2945, 2858, 1727, 1685, 1538, 1424, 1371, 1287, 1225, 1113 wavenumber (cm$^{-1}$). GPC data was reported as follows: MN=91,800 g/mol, MW=119,000 g/mol, PDI=1.3. A second peak was observed that seems to correspond to excess PVP-OH; MN=5570, MW=7860. The following spectral properties were observed by $^{13}$C NMR (CDCl$_3$): δ175, 78.5, 76.5, 75.8, 72.4, 70.6, 68.7, 28.1, 26.4, 24.7, 18.3.

Example 4

Dip Coating of PVP-Polyurethane-PVP Block Copolymer in NMP

MATERIALS: The triblock copolymer synthesized as in Example 3 was used along with N-methyl-2-pyrrolidinone (NMP) received from Aldrich. PELLETHANE 75D polyurethane pellets, obtained from Dow Chemical, Midland, Mich., were dried under full vacuum at 80° C. for eighteen hours. The pellets were then pressed into 1.02 mm thick sheets at 230° C., using a Carver, Inc. Press, Model #2699. The PELLETHANE 75D sheets were then cut into 2.5 cm by 10.2 cm strips for dip coating tests.

PROCEDURE: In a 50-mL round-bottomed flask, 0.06 g of the triblock copolymer of Example 3 was dissolved into 3.88 g NMP solvent, making a 1.5% polymer solution. A PELLETHANE sample was dipped in the polymer/NMP solution for approximately 15 seconds. The sample was hung to dry in a 70° C. oven for eighteen hours. The sample was then placed in a vial of water and placed on the shaker table for 20 minutes. The sample was slippery to the touch, relative to the uncoated substrate. The coating was slightly opaque and pale yellow in color. The coating did not rub off the substrate.

Example 5

Synthesis of Isocyanate-Teminated B-block Prepolymer

MATERIALS: QO POLYMEG 1000 (PTMO) was purchased from Penn Specialty Chemicals, Inc., Memphis, Tenn. The PTMO was dried under full vacuum at 100° C. Flaked MONDUR M (MDI) was purchased from Bayer Corporation and stored in a freezer until use. Anhydrous dioxane was purchased from Aldrich and was used as received.

SYNTHESIS: Inside a nitrogen atmosphere glove box, 15.7 g (15.43 mmol) PTMO and 80 g anhydrous dioxane were added to a 3-neck 250-mL round-bottomed flask equipped with magnetic stir bar, thermocouple, and air condenser for gas expansion. The solution was stirred and allowed to equilibrate at 70° C. before 4.33 g (17.21 mmol) MDI was added to the reaction vessel. A small drop, approximately 75 parts per million (ppm), of tin dilaurate catalyst was added. The reaction mixture was heated up to 93° C. briefly and the remainder of the reaction was run at 74° C. The reaction was run overnight and the viscosity was noticeably higher the next morning.

The reaction was monitored by IR spectroscopy. The NCO peak at 2270 cm$^{-1}$ was initially very strong and there was a broad absorption around 3500 cm$^{-1}$, corresponding to the PTMO hydroxyl groups. Almost immediately after adding the catalyst, the absorption around 3500 cm$^{-1}$ was gone and a new broad peak around 3300 cm$^{-1}$ formed, indicating urethane bond formation. A small isocyanate peak at 2270 cm$^{-1}$ remained, indicating the prepolymer was isocyanate-terminated. The isocyanate groups of the prepolymer were quenched with ethanol prior to GPC analysis. The molecular weight results by GPC were: MN=47,200 g/mol, MW=73,500 g/mol, PDI=1.56. The following spectral properties were observed by $^{13}$C NMR (CDCl$_3$): δ153.9, 136.3, 136.1, 129.4, 118.8, 70.7, 70.6, 70.19, 40.58, 26.5, 26.23, 25.9.

Example 6

Synthesis of Hydroxyl-Terminated Poly(N-vinylpyrrolidone)

MATERIALS: The monomer N-vinylpyrrolidone was purchased from Aldrich and the NaOH inhibitor was removed by vacuum distillation. The monomer was stored in a freezer prior to use. All other reagents were used as received from Aldrich, including: anhydrous diethyl ether, 2,2-azobisisobutyronitrile (AIBN), and the chain transfer agent 2-isopropoxyethanol.

SYNTHESIS: In an oven-dried, nitrogen purged 12-liter (L) 3-neck round-bottomed flask equipped with a magnetic stir bar, thermocouple, oil bubbler, heating mantle, and 500-mL addition flask, 800 g N-vinylpyrrolidone was mixed with 4558.25 g (5.04 L) isopropoxyethanol chain transfer agent. Nitrogen gas was bubbled through the reaction solution for 24 hours with stirring. More isopropoxyethanol, 494.19 g (547 mL), was used to dissolve 2.902 g AIBN. The AIBN solution was purged within the addition flask for one hour as the bulk reaction solution was slowly heated to 80° C. The stop-cock of the addition flask was then opened, to add the purged AIBN solution to the 80° C. reaction solution. The nitrogen sparge tube was pulled out of the reaction solution to purge the overhead space for the duration of the reaction. The reaction mixture was heated for 24 hours. The roto-evaporator was set up to directly add the reaction solution into the 3-L round-bottomed flask being rotated.

The isopropoxyethanol was evaporated at 50° C. and 18 mm Hg (2.4 kPa) until there was 1,505.4 g left in the round-bottomed flask. This concentrated solution was poured into a Waring blender containing cold ether. With fast stirring, a white precipitate formed and was collected by filtration on in a Buchner funnel. The product was a white powder. The white powder was purified in a Soxhlet extraction set up containing 500 mL ether. The extractions were run for 72 hours. The product was dried under vacuum at 50° C. for three days to remove the ether.

The molecular weight data obtained by GPC was as follows: MN=19,200 g/mol, MW=36,400 g/mol, PDI=1.90. The hydroxyl functionality was confirmed by reacting the PVP-OH with an isocyanate-terminated prepolymer made of MDI and PTMO, as in example 2. The isocyanate peak at 2270 cm$^{-1}$ that was present in the prepolymer IR spectrum disappeared upon the addition of the PVP-OH. New peaks corresponding with urethane linkages at 3266 cm$^{-1}$ and 1727 cm$^{-1}$ were present in the IR spectrum of the product. This data supports that the poly(vinyl pyrrolidone) was hydroxyl-terminated.

Example 7

Synthesis of PVP-Polyurethane-PVP Block Copolymer

MATERIALS: Hydroxyl-terminated poly(N-vinyl pyrrolidone) (PVP-OH) was synthesized as described in Example 6. Prior to this reaction the PVP-OH was dried under full vacuum at 50° C. for two days. The isocyanate-terminated B-block prepolymer was synthesized as described in Example 5. Anhydrous Dioxane and anhydrous dimethylacetamide (DMAC) were purchased and used as received.

SYNTHESIS: Inside a nitrogen atmosphere glove box, 5.08 g PVP-OH was dissolved in 20.1 g anhydrous DMAC in a dry 30 milliliter (4-ounce) glass jar. Next, 25.44 g of 20% solution of the B-block prepolymer in dioxane solution was added to the reaction vessel. The reaction mixture was shaken and placed in a 60° C. oven inside the nitrogen glove box for eighteen hours. The reaction was monitored by IR spectroscopy. The isocyanate peak at 2270 cm$^{-1}$ that was present in the prepolymer spectrum disappeared upon the addition of the PVP-OH. New peaks corresponding with urethane linkages at 3266 cm$^{-1}$ and 1727 cm$^{-1}$ were present in the spectrum of the product.

Example 8

Dip Coating of PVP-Polyurethane-PVP Block Copolymer in NMP

MATERIALS: The PVP-PU-PVP triblock copolymer synthesized as in Example 7 was used along with N-methyl-2-pyrrolidinone (NMP) received from Aldrich. PELLETHANE 75D pellets were dried under full vacuum at 80° C. for eighteen hours. The pellets were then pressed into 1.02 mm thick sheets at 230° C., using a Carver, Inc. Press, Model #2699. The PELLETHANE 75D sheets were then cut into 2.5 cm by 10.2 cm strips for dip coating tests.

PROCEDURE: In a 250-mL round-bottomed flask, 30.52 g of the PVP-PU-PVP triblock copolymer was dissolved into approximately 100 mL NMP solvent, making a 30% polymer solution. A PELLETHANE sample was dipped in the polymer/NMP solution for approximately 15 seconds. The sample was hung to dry in a 70° C. oven for eighteen hours and was then rinsed in water. The sample was slippery to the touch, relative to the uncoated substrate. The coating was slightly opaque and pale yellow in color. The coating did not rub off the substrate.

Example 9

Dip Coating of PVP-Polyurethane-PVP Block Copolymer in NMP

MATERIALS: The PVP-PU-PVP triblock copolymer synthesized as in Example 7 was used along with N-methyl-2-pyrrolidinone (NMP) received from Aldrich. GRILAMID (Nylon 11, sold by EMS-GRIVORY, Sumter, S.C.) pellets, were dried under full vacuum at 80° C. for eighteen hours. The pellets were then pressed into 1.02 mm thick sheets at 230° C., using a Carver Inc. Press, Model #2699. The PELLETHANE 75D sheets were then cut into 2.5 cm by 10.2 cm strips for dip coating tests.

PROCEDURE: In a 250-mL round-bottomed flask, 30.52 g of the PVP-PU-PVP triblock copolymer was dissolved into approximately 100 mL NMP solvent, making a 30% polymer solution. A GRILAMID sample was dipped in the polymer/NMP solution for approximately 15 seconds. The sample was hung to dry in a 70° C. oven for eighteen hours and was then rinsed in water. The sample was slippery to the touch, relative to the uncoated substrate. The coating was slightly opaque and pale yellow in color. The coating did not rub off the substrate.

Example 10

Synthesis of Isocyanate-Terminated B-block Prepolymer

MATERIALS: QO POLYMEG 1000 (PTMO) was purchased from Penn Specialty Chemicals, Inc. The PTMO was dried under full vacuum at 100° C. Flaked MONDUR M (MDI) was purchased from Bayer Corp. and stored in a freezer until use. Anhydrous dioxane was purchased from Aldrich and was used as received.

SYNTHESIS: Inside a nitrogen-atmosphere glove box, 156.75 g (153.6 mmol) PTMO and 800.04 g anhydrous dioxane were added to a 3-neck 2-liter round-bottomed flask equipped with magnetic stir bar, thermocouple and air condenser for gas expansion. The solution was stirred and allowed to equilibrate at 78° C. before 43.25 g (171.7 mmol) MDI was added to the reaction vessel. A small drop of tin dilaurate catalyst was added. The reaction mixture was heated for eighteen hours at 82° C. The viscosity was noticeably higher the next day.

The reaction was monitored by IR spectroscopy. The NCO peak at 2270 cm$^{-1}$ was initially very strong and there was a broad absorption around 3500 cm$^{-1}$, corresponding to the PTMO hydroxyl groups. Upon completion of the reaction, the absorption around 3500 cm$^{-1}$ was gone and a new broad peak around 3300 cm$^{-1}$ formed, indicating urethane bond formation. A small isocyanate peak at 2270 cm$^{-1}$ remained, indicating the prepolymer was isocyanate-terminated.

Example 11

Synthesis of PVP-Polyurethane-PVP Block Copolymer

MATERIALS: Hydroxyl-terminated poly(N-vinyl pyrrolidone) (PVP-OH) was synthesized as described in Example 6. Prior to this reaction the PVP-OH was dried under full vacuum at 50° C. for two days. The isocyanate-terminated B-block prepolymer was synthesized as described in Example 10. Anhydrous dioxane and anhydrous dimethylacetamide (DMAC) were purchased and used as received.

SYNTHESIS: Inside a Nitrogen atmosphere glove box, 198.87 g PVP-OH was dissolved in 794.79 g anhydrous DMAC in a dry 3-liter 3-neck round-bottomed flask. The flask was placed in a 60° C. oven inside the dry box until the PVP-OH dissolved. The entire prepolymer batch synthesized in Example 10 was transferred to the 3-neck round-bottomed flask containing the PVP-OH in DMAC. The reaction mixture was magnetically stirred and heated with a heating mantle and temperature controller set at 65° C. for eighteen hours. The reaction was monitored by IR spectroscopy. The isocyanate peak at 2270 cm$^{-1}$ that was present in the prepolymer spectrum disappeared upon the addition of the PVP-OH. New peaks corresponding with urethane linkages at 3266 cm$^{-1}$ and 1727 cm$^{-1}$ were present in the spectrum of the product.

The block copolymer was precipitated using cold ether and a Waring blender. First, the polymer solution was poured into the blender. Next, cold ether was slowly added to the polymer solution with fast stirring. Once a cloudy suspension formed, more ether was quickly added to precipitate the polymer. The final ratio by volume was 4:1 ether to polymer solution. The block copolymer formed very small particles that were small enough to go through filter paper. The suspension was allowed to settle out for 5 to 10 minutes, enabling the particles to coalesce. The polymer was then able to be filtered through a large mesh. Mesh was used because regular filter paper immediately became clogged. Being both hydrophilic and hydrophobic, the polymer still retained a lot of the solvent. The polymer was scraped from the mesh into a pan lined with MYLAR film. The pan was placed into a vacuum oven equipped with a cold trap to further remove the solvent. The temperature of the oven was set at 50° C. and a full vacuum was pulled. Once the full vacuum was applied, the nitrogen was turned on so the resulting pressure was 52 mm Hg (1.0 pound per square inch (psi) above the full vacuum, 6.93 kPa) to create some flow within the chamber to aid in solvent removal. After eighteen hours, the polymer was a semi-hard sheet. The sheet of polymer was placed in a mesh bag, submerged into liquid nitrogen, and broken with a mallet into pieces small enough to fit in the grinder. The polymer was ground into small pellets and placed back into a MYLAR-lined pan and into the vacuum oven to remove any remaining solvent. The oven temperature was increased to 60° C. and the polymer dried under vacuum with 52 mm (Hg (1 psi), 6.93 kPa) nitrogen purge for 72 hours. The yield of the final block copolymer product was 230 g, corresponding to a 57.7% yield.

The following spectral properties were observed by $^{13}$C NMR (CDCl$_3$): δ175.3, 153.9, 136.1, 129.4, 118.9, 70.6, 70.19, 64.9, 44.9, 43.6, 42.0, 40.5, 31.5, 26.5, 26.2, 25.8, 18.3. The following spectral properties were observed by proton NMR (CDCl$_3$): δ7.0, 4.1, 3.3, 3.1, 2.6, 2.2, 2.0, 1.64, 1.5, 1.3.

Example 12

Synthesis of a Citric Acid Triester

A 250-mL three-neck round-bottomed flask is outfitted with a magnetic stirbar and thermocouple. A Dean-Stark trap is placed in the central neck, and a condenser is connected to the trap. The assembled glassware is placed in a heating mantle on a stirplate, and 192 milligrams (0.01 mole) citric acid is added to the flask, followed by three equivalents (0.03 mole) of hydroxy-terminated PVP, 10 milligrams para-toluenesulfonic acid and 100 milliliters of toluene. The reaction mixture is stirred magnetically and heated to 50° C. Ten drops of concentrated sulfuric acid is added, and the reaction mixture is brought to reflux. When no further water is collected in the trap, the flask contents are cooled to room temperature. The solid product is collected by vacuum filtration.

Example 13

Synthesis of a Block Copolymer Based on the Citric Acid Triester

Ten grams of the triester synthesized in Example 12 are placed in a dry 250-mL three-neck round-bottomed flask outfitted with a magnetic stirbar and a nitrogen inlet connected to a bubbler. The nitrogen flow is started, and 100 mL anhydrous tetrahydrofuran is added. Stirring is started and when the triester has dissolved, the tetrahydrofuran solution is transferred via cannula to a stirred flask containing a stoichiometric amount of isocyanate-terminated prepolymer (made using POLYMEG and MDI, as in the previous examples). The mixture is heated to 60° C. and stirring is continued until the reaction is complete as measured by disappearance of the isocyanate absorption peak at 2270 reciprocal centimeters (cm$^{-1}$). The solvent is removed using a rotary evaporator.

Example 14

One Step Synthesis of a PVP-PU-PVP Block Copolymer

MATERIALS: The hydroxyl-terminated poly(N-vinylpyrrolidone) synthesized in Example 6 was used after drying under vacuum at 50° C. QO POLYMEG 1000 (PTMO) was purchased from Penn Specialty Chemicals, Inc. The PTMO was dried under full vacuum at 100° C. Flaked MONDUR M (MDI) was purchased from Bayer Corporation and stored in a freezer until use. Anhydrous dioxane was purchased from Aldrich and was used as received.

SYNTHESIS: In a 250-mL dried round-bottomed flask, equipped with a magnetic stirbar and thermocouple, 5.03 g of hydroxyl terminated poly(vinyl pyrrolidone) and 3.96 g POLYMEG 1000 were mixed with 20.12 g anhydrous dioxane and 20.12 g anhydrous DMAC. A small drop of tin dilaurate catalyst was added after an initial IR scan was taken. After the solution was heated to 70° C., 1.29 g MDI was added. The solution changed from colorless to light yellow in color. After a few minutes, the solution turned darker yellow. The solution became noticeably more viscous as the reaction progressed. The progress of the reaction was monitored by IR spectroscopy. After eighteen hours of reaction time, the NCO peak was no longer present in the IR spectrum, but the hydroxyl peak remained. An additional 0.23 g MDI was added to the solution and allowed to react for 24 hours. The IR spectrum showed the hydroxyl peak remained unchanged, but the NCO peak disappeared. The solution was cooled to room temperature and precipitated into approximately 800 mL of cold ether. The polymer formed yellow-white granules, which were placed in a vacuum oven at 50° C. to remove residual solvent. A total of 8.58 g of polymer was collected, corresponding to an 81.6% yield.

The GPC data was as follows: MN=24,800 g/mol, MW=64,700 g/mol, PDI=2.61. The molecular weight results correspond well with a block copolymer made with the two-step method.

The following spectral properties were observed by $^{13}$C NMR (CDCl$_3$): δ175.3, 153.9, 136.1, 129.4, 118.9, 70.6, 70.19, 64.9, 44.9, 43.6, 42.0, 40.5, 31.5, 26.5, 26.2, 25.8, 18.3. The following spectral properties were observed by proton NMR (CDCl$_3$): δ7.0, 4.1, 3.3–3.8 (broad), 3.1 (broad), 2.2, 2.0 (broad), 1.72, 1.64, 1.5, 1.3. The NMR spectra correspond well with NMR spectra of block copolymers made with the two-step synthesis route.

Example 15

Dip Coating Using the PVP-PU-PVP Block Copolymer Synthesized by the One Step Method MATERIALS: The PVP-PU-PVP triblock copolymer synthesized by the one step method as in Example 14 was used along with N-methyl-2-pyrrolidinone (NMP) received from Aldrich. PELLETHANE 75D pellets were dried under full vacuum at 80° C. for eighteen hours. The pellets were then pressed into 0.1 cm (0.04 inch) thick sheets at 230° C., using a Carver Inc. Press, Model #2699. The PELLETHANE 75D sheets were then cut into 2.54 cm (one inch) by 10.2 cm (4 inch) strips for dip coating tests.

PROCEDURE: In a glass jar, a 20% solids solution was created by dissolving 1.31 g of the PVP-PU-PVP triblock copolymer in 5.2 g NMP solvent. A PELLETHANE sample was dipped in the polymer/NMP solution for approximately 15 seconds. The sample was hung to dry in a 70° C. oven for eighteen hours. The sample was rinsed with water and the coating turned opaque white. The coated area was slippery to the touch, relative to the uncoated substrate. The slip coating did not rub off the substrate.

Example 16

Synthesis of a Hydroxy-Terminated Copolymer of 1-Vinyl-2-pyrrolidone and Methyl Acrylate Five grams 1-vinyl-2-pyrrolidone (purified as noted previously in Example 1) and one gram methyl acrylate (vacuum distilled from calcium hydride) are placed in a three-neck one-liter flask outfitted with a stirbar, sparge tube, thermocouple, and rubber septum. Then 500 mL 2-isopropoxyethanol are added. The flask is placed in a heating mantle on a stirplate, and the contents are stirred magnetically. The reaction mixture is sparged with nitrogen for 60 minutes. The reaction mixture is heated to 80° C. during the sparging. Five hundred milligrams AIBN is dissolved in 10 mL 2-isopropoxyethanol in a septum-capped vial and this solution is also sparged during this time (done by placing a hypodermic needle attached to a nitrogen line through the septum into the solution and an additional needle through the septum with its tip above the solution). When sparging is complete and the large flask has reached the indicated temperature, the sparge tube is raised above the solution meniscus and the vial contents are transferred to the flask under nitrogen pressure using a double-ended needle. The contents are stirred at 80° C. for 24 hours. The 2-isopropoxyethanol is removed by rotary evaporation, leaving a concentrated solution of approximately 25 mL volume. The polymer is then isolated as described in Example 1.

Example 17

Synthesis of a Carboxylic Acid-Functionalized Chain Transfer Agent

Five hundred grams of anhydrous 2-propanol (Aldrich) is added to a dry 2-L three-neck round-bottomed flask outfitted with a magnetic stirbar, addition funnel, nitrogen inlet connected to a bubbler, and thermocouple. Five hundred milligrams of sodium are added and stirred for one hour. Acrylonitrile (442 grams, one equivalent) is added dropwise. The reaction mixture is stirred overnight. The product is then added to chloroform and washed sequentially with dilute aqueous HCl, saturated aqueous sodium bicarbonate, and deionized water. The chloroform solution is then dried over anhydrous magnesium sulfate. The chloroform is removed using a rotary evaporator, and the crude product distilled. A portion of the resulting 2-cyanoethoxy-2-propane is dissolved in dry methanol acidified with HCl, and the solution is refluxed for four hours. The excess methanol is removed under vacuum using a rotary evaporator, and the crude ester then distilled under vacuum. This ester can be used as a chain transfer agent, or it may be hydrolyzed to yield the desired 2-carboxyethoxy-2-propane.

Example 18

Synthesis of an Amine-Functionalized Chain Transfer Agent

A portion of the 2-cyanoethoxy-2-propane prepared above is reduced by heating at 70° C. with lithium aluminum hydride (0.5 M in diglyme, Aldrich) overnight. The resulting solution is cooled to room temperature and poured on to ice. The mixture is extracted three times with chloroform. The chloroform solution is washed with distilled water and then dried over anhydrous magnesium sulfate. The solvent is removed by rotary evaporation and the crude product distilled under vacuum.

Example 19

Synthesis of an Amide-Functionalized Chain Transfer Agent

A portion of the 2-cyanoethoxy-2-propane prepared above is converted to the corresponding amide by heating at 50° C. in concentrated hydrochloric acid (HCl) for one hour. The mixture is then cautiously poured into a large volume of ice water, which is extracted with chloroform. The chloroform solution is washed twice with saturated aqueous sodium bicarbonate, then with deionized water. The chloroform is removed using a rotary evaporator.

Example 20

Synthesis of a Silane-Functionalized Chain Transfer Agent

Five hundred grams isopropyl vinyl ether (prepared by the method of Adelman as reported in the *Journal of the American Chemical Society*, volume 75, pp. 2678–82 (1953)) is placed in a five-liter 3-neck flask outfitted with a magnetic stirbar, condenser, thermocouple, and addition funnel. One milliliter platinum hydrosilylation catalyst solution (United Chemicals, Bristol, Pa., is added to the flask. Triethoxysilane (955 grams, 1 equivalent) is added to the addition funnel. The contents of the flask are heated to 50° C. The heating mantle is turned off and the triethoxysilane is added at a rate such that a gentle reflux is maintained. After addition is complete, the reaction mixture is allowed to stir overnight. The platinum catalyst is removed using an amine-functionalized ion-exchange resin (AMBERLITE IRC-718), followed by passing the product through a column containing neutral alumina. The crude 2-(triethoxysilyl)ethoxy-2-propane is then distilled under vacuum.

Example 21

Synthesis of PVP-PU-PVP with a Segmented Polyurethane Block

MATERIALS: QO POLYMEG 1000 (PTMO) was purchased from Penn Specialty Chemicals, Inc. The PTMO was dried under full vacuum at 100° C. Flaked MONDUR M (MDI) was purchased from Bayer Corporation and stored in a freezer until use. Butane diol (BDO) was purchased from Aldrich and was dried under full vacuum at 60° C. Anhydrous dioxane was purchased from Aldrich and was used as received.

SYNTHESIS: Inside a nitrogen-atmosphere glove box, 0.70 g BDO, 7.86 g PTMO and 51.50 g anhydrous dioxane were added to a 3-neck 500-mL round-bottomed flask equipped with magnetic stir bar, thermocouple, and air condenser for gas expansion. The solution was stirred and allowed to equilibrate at 78° C. before 4.34 g MDI and one drop of tin dilaurate catalyst was added to the reaction vessel. The reaction mixture was heated for eighteen hours at 72° C.

The reaction was monitored by IR spectroscopy. The NCO peak at 2270 cm$^{-1}$ was initially very strong and there was a broad absorption around 3500 cm$^{-1}$, corresponding to the PTMO hydroxyl groups. Upon completion of the reaction, the absorption around 3500 cm$^{-1}$ was gone and a new broad peak around 3300 cm$^{-1}$ formed, indicating urethane bond formation. A large isocyanate peak at 2270 cm$^{-1}$ remained, indicating the prepolymer was isocyanate-terminated. The molecular weight of this prepolymer was determined by GPC relative to polystyrene standards. The MN=5900 g/mol, MW=11,100 g/mol, and the PDI was 1.88.

Hydroxyl-terminated poly(vinyl pyrrolidone) (PVP-OH), totaling 65.86 g, and 259.10 g anhydrous DMAC were mixed in a large glass vessel and placed in a 60° C. oven to help the PVP-OH into solution. The PTMO/BDO prepolymer was transferred to a dry 1-liter 3-neck flask. The PVP-OH/DMAC solution was added to the 1-liter round-bottomed flask and was also used to rinse out the 500-mL round-bottomed flask. The reaction was monitored by IR, and the isocyanate peak disappeared within two hours. The polymer was precipitated into a total of 2.5 liters of cold ether. The yellow-white precipitate was filtered out in a Buchner funnel and placed in a MYLAR-lined pan to dry under vacuum at 60° C. overnight. The yield was 48.79 g, corresponding to a 60.8% yield. The molecular weight of this block copolymer was determined by GPC relative to polystyrene standards.

The MN=16,300 g/mol, MW=34,500 g/mol, and the PDI was 2.12.

Example 22

Dip Coating Using the PVP-PU-PVP Block Copolymer with Segmented Polyurethane Block MATERIALS: The PVP-PU-PVP triblock copolymer with segmented polyurethane block, synthesized as in Example 21, was used along with N-methyl-2-pyrrolidinone (NMP) received from Aldrich. PELLETHANE 75D (segmented polyurethane sold by Dow Chemical, Midland, Mich.) pellets were dried under full vacuum at 80° C. for eighteen hours. The pellets were then pressed into 0.1 cm (0.04 inch) thick sheets at 230° C., using a Carver Inc. Press, Model #2699. The PELLETHANE 75D sheets were then cut into 2.54 cm (one inch) by 10.2 cm (4 inch) strips for dip coating tests.

PROCEDURE: In a glass jar, a 20% solids solution was created by dissolving 0.47 g segmented triblock copolymer in 1.8 g NMP solvent. A PELLETHANE sample was dipped in the polymer/NMP solution for approximately 15 seconds. The sample was hung to dry in a 70° C. oven for eighteen hours. The sample was rinsed with water and the coated area was found to be slippery to the touch, relative to the uncoated substrate.

Although some of the coating rubbed off, the base layer remained and was slippery.

Example 23

Synthesis of an Isocyanatotelechelic Polyamide

A dry two-liter round-bottomed three-neck flask is outfitted with a thermocouple, addition funnel, and condenser. A nitrogen inlet connected to a bubbler is placed on top of the condensor and the flask is purged with nitrogen. One liter of anhydrous DMAC and fifty grams of diisocyanatohexane are added to the flask. Ten drops of dibutyltin dilaurate is added to the flask. The contents of the flask are heated to 70° C. with stirring. Sixty grams of 1,12-dodecanedioic acid are dissolved in a minimal amount of DMAC and the resulting solution is transferred to the addition funnel. The contents of the addition funnel are added dropwise, and the reaction stirred overnight. The product of the reaction is used without isolation, as described below.

Example 24

Synthesis of a PVP-Polyamide-PVP Block Copolymer

To the solution of isocyanatotelechelic polyamide synthesized in Example 23 is added two equivalents of hydroxy-terminated PVP. Progress of the reaction is monitored by observing the disappearance of the isocyanate band in the IR at about 2270 cm$^{-1}$. The resulting polymer solution can be used as a polymer coating without isolation.

Example 25

Synthesis of an Isocyanatotelechelic Poly(amide-ether)

To the solution of the isocyanatotelechelic polyamide created in Example 23 is added 18 grams POLYMEG (molecular weight 1000 g/mol). The reaction mixture is stirred an additional two hours at 70° C. and used directly in the following example.

Example 26

Synthesis of a PVP-Poly(amide ether)-PVP Block Copolymer

To the solution of isocyanatotelechelic poly(amide-ether) synthesized above in Example 25 is added two equivalents of hydroxy-terminated PVP. Progress of the reaction is monitored by observing the disappearance of the isocyanate band in the IR at about 2270 cm$^{-1}$. The resulting polymer solution can be used as a polymer coating without isolation.

Example 27

Alternative Synthesis of a PVP-Poly(amide-ether)-PVP Block Copolymer

A dry three-neck one-liter round-bottomed flask is outfitted with a heating mantle, stirbar, condenser, and thermocouple. A nitrogen inlet connected to a bubbler is placed on the condenser. Five hundred milliliters anhydrous dioxane is added to the flask, followed by 60 grams of bis (carboxymethoxy) polyethylene glycol (Aldrich) and one drop dibutyltin dilaurate. The contents of the flask are stirred magnetically and heated to 50° C., then 27.53 grams of MDI are added to the flask. The mixture is brought to reflux and stirred eighteen hours, then 192 grams hydroxy-terminated PVP is added. The mixture is then stirred 24 hours. The polymer is precipitated into cold ether and dried in a vacuum oven at 50° C.

Example 28

Synthesis of an Isocyanatotelechelic Block Containing Imide Groups and Incorporation into an A-B-A Block Copolymer A dry three-neck three-liter round-bottomed flask is outfitted with a heating mantle, stirbar, condenser with Dean-Stark trap, and thermocouple. A nitrogen inlet connected to a bubbler is placed on the condenser. Two liters anhydrous m-cresol is added to the flask, followed by 218 grams 1,8-diaminooctane, 48 grams pyromellitic anhydride, and 500 milligrams isoquinoline. The reaction is stirred and heated to reflux for 8 hours. The product is precipitated by pouring into a large excess of cold, stirred methanol and vacuum filtered. It is washed with additional cold methanol and then dried under vacuum. Ten grams of this product is placed in a dry three-neck one-liter flask outfitted with a heating mantle, stirbar, condenser, and thermocouple. Five hundred milliliters anhydrous N,N-dimethylacetamide is then placed in the flask, followed by one drop dibutyltin dilaurate and 19.2 grams of hydroxy-terminated PVP of molecular weight 19,200 g/mol. The mixture is heated to 50° C. with stirring, then 17.8 grams MDI are added. The reaction mixture is stirred overnight at 50° C. This solution can be used as a polymer coating with isolation. The polymer is isolated by pouring the solution into a large excess of cold, stirred methanol. The product is filtered, washed with additional cold methanol, and dried under vacuum.

Example 29

Synthesis of a PVP-Polyurea-PVP Block Copolymer

A dry three-neck one-liter round-bottomed flask is outfitted with a heating mantle, stirbar, condenser, and thermocouple. To the flask is added 500 milliliters dioxane, one drop dibutyltin dilaurate, and 20 g bis(3-aminopropyl) terminated polytetrahydrofuran (Aldrich).

The contents of the flask are heated to 50° C. and 17.5 g MDI is added. After 4 hours, 19.2 g hydroxy-terminated PVP is added to the reaction mixture, and stirring is continued at 50° C. overnight. The resulting polymer solution can be used as a polymer coating without isolation.

Example 30

Synthesis of a PVP-Polyester-PVP Block Copolymer

MATERIALS: Hydroxyl-terminated poly(vinyl pyrrolidone) (PVP-OH) was used as synthesized in Example 6. DMAC (anhydrous) and tolylene-2,4-diisocyanate terminated poly(ethylene adipate) (MN approximately 2700 g/mol) were purchased from Aldrich and used as received.

PROCEDURE: Into a dry 500-mL 3-neck round-bottomed flask, equipped with magnetic stirbar, thermocouple and condenser, 108.05 g anhydrous DMAC and 1.38 g tolylene-2,4-diisocyanate terminated poly(ethylene adipate) were mixed and heated to 70° C. PVP-OH was added in batches of about 5 g until the NCO peak was no longer visible by IR. A total of 9.95 g PVP-OH was added in total. The solution was heated for eighteen hours. Half of the reaction solution was then used to precipitate the polymer into 1.5 liters (L) of cold ether. The other half was kept in the reaction solution. The precipitate was a white powder that turned yellow and sticky within minutes. This was placed under vacuum to dry for 48 hours. The polymer was reprecipitated into 0.5 L cold ether, and placed back under vacuum to dry. A total of 5.22 g of the PVP-Polyester-PVP block copolymer was isolated.

Example 31

Dip Coating using the PVP-Polyester-PVP Block Copolymer

MATERIALS: The PVP-Polyester-PVP Block Copolymer, synthesized as in Example 30, was used along with N-methyl-2-pyrrolidinone (NMP) received from Aldrich. PELLETHANE 75D (segmented polyurethane sold by Dow Chemical, Midland, Mich.) pellets were dried under full vacuum at 80° C. for eighteen hours. The pellets were then pressed into 0.1 cm (0.04 inch) thick sheets at 230° C., using a Carver Inc. Press, Model #2699. The PELLETHANE 75D sheets were then cut into 2.54 cm (one inch) by 10.2 cm (4 inch) strips for dip coating tests.

PROCEDURE: In a glass jar, a 20% solids solution was created by dissolving 0.389 g PVP-Polyester-PVP block copolymer in 1.54 g NMP solvent. A PELLETHANE sample was dipped in the polymer/NMP solution for approximately 15 seconds. The sample was hung to dry in a 70° C. oven for eighteen hours. The sample was rinsed with water and the coating turned opaque white. The coated area was slippery to the touch, relative to the uncoated substrate.

Example 32

Synthesis of a PVP-Polyester-PVP Block Copolymer Containing BDO in the Polyester Segment Materials: Hydroxyl-terminated poly(vinyl pyrrolidone) (PVP-OH) was used as synthesized in Example 6. DMAC (anhydrous) and tolylene-2,4-diisocyanate terminated poly (ethylene adipate) (MN approximately 2700 g/mol) were purchased from Aldrich and used as received. Butane diol (1,4) (BDO) was purchased from Aldrich and was dried under full vacuum at 60° C.

Procedure: Into a dry 500-mL 3-neck round-bottomed flask, equipped with magnetic stirbar, thermocouple, and condenser, 132.02 g anhydrous DMAC, 0.35 g BDO, and 10.04 g tolylene-2,4-diisocyanate terminated poly(ethylene adipate) were mixed and heated to 70° C. An IR taken after 20 minutes showed that all the hydroxyl groups had reacted, and an NCO peak remained. A total of 6.03 g PVP-OH was then added and the solution was heated at 70° C. for eighteen hours. The IR showed no remaining NCO peak and a small peak related to excess hydroxyl. The polymer was then precipitated into a blender containing cold ether. A total of 1.5 liters of ether was used in the precipitation. The polymer was stringy, unlike the powder that formed in the PVP-polyester-PVP synthesis that did not contain BDO. This could be an indication of higher molecular weight. The product was placed under vacuum at 50° C. to dry for 48 hours. A total of 12.46 g of the BDO-containing PVP-Polyester-PVP block copolymer were isolated, corresponding to a 76% yield.

Example 33

Dip Coating using the PVP-Polyester-PVP Block Copolymer Synthesized with BDO

MATERIALS: The PVP-Polyester-PVP Block Copolymer containing BDO, synthesized as in Example 32, was used along with N-methyl-2-pyrrolidinone (NMP) received from Aldrich. PELLETHANE 75D (segmented polyurethane sold by Dow Chemical, Midland, Mich.) pellets were dried under full vacuum at 80° C. for eighteen hours. The pellets were then pressed into 0.1 cm (0.04 inch) thick sheets at 230° C., using a Carver Inc. Press, Model #2699. The PELLETHANE 75D sheets were then cut into 2.54 cm (one inch) by 10.2 cm (4 inch) strips for dip coating tests.

PROCEDURE: In a glass jar, a 20% solids solution was created by dissolving 0.459 g block copolymer in 1.84 g NMP solvent. A PELLETHANE sample was dipped in the polymer/NMP solution for approximately 15 seconds. The sample was hung to dry in a 70° C. oven for eighteen hours. The sample was rinsed with water and the coating turned opaque white. The coated area was slippery to the touch, relative to the uncoated substrate.

Example 34

Lubricity of a Polymer with a PVP-PU-PVP Block Copolymer Coating

An Imass Slip/Peel Tester Model SP-2000 was used to obtain quantitative data regarding the lubricity of the block copolymer coating. The coefficient of friction (COF) was measured for uncoated GRILAMID (Nylon 11) sheets and GRILAMID (Nylon 11) sheets coated with the block copolymer. The coating was applied to the GRILAMID (Nylon 11, sold by EMS-GRIVORY, Sumter, S.C.) sheets (after initial COF measurements) by dipping the sample into a solution of 20% block copolymer in NMP, followed by hanging the sample in a 70° C. oven for eighteen hours.

The ASTM method D-1894 was used as a guide for the determination of the coefficient of friction. The coefficient of friction is the ratio of the normal force (weight of the sled) over the tractive force, which is the force required to initiate and maintain relative motion between the surfaces. The GRILAMID surface was tested against PEBAX material (polyamide ether copolymer, sold by ATOFINA, Blooming Prairie, Minn.), which was attached to the 200 g sled. The GRILAMID surface was kept wet with deionized water throughout the duration of the sled test. The instrument was set with the following parameters: 5 kg cell, 200 g sled (scaled to 208.6 g with the attached PEBAX), 2 second delay, 31 mm (1.22 inch) distance, 10 seconds averaging, 152 mm/minute (6 inch/minute) speed. Five sled test runs were performed on the coated GRILAMID sheet and four runs were performed on the uncoated sheet. The results of the runs were averaged and are reported in the table below.

The static peak is defined as the maximum COF that occurs during the delay time. The kinetic peak is the maximum COF that occurs during the averaging time, while the valley reports the lowest COF measured during the averaging time. The reported average is an average of the COF measured during the ten second averaging time, and the root mean squared (RMS) shows the deviation from the average value.

|  | GRILAMID Uncoated | GRILAMID Coated |
| --- | --- | --- |
| Static Peak | 0.249 | 0.064 |
| Kinetic Peak | 0.206 | 0.024 |
| Valley | 0.147 | 0.002 |
| *Average | 0.175 | 0.006 |
| RMS | 0.011 | 0.003 |

The block copolymer coating decreased the average COF by more than 50% compared to the uncoated substrate.

Example 35

Preparation of Coextruded Tubing with a PVP-PU-PVP Copolymer Coating on the Surface of the Inner Lumen A lubricious copolymer was coextruded with PELLETHANE 55D (PL55D) polyurethane pellets (obtained from Dow Chemical Co.) into tubing form. The PELLETHANE pellets were extruded with a single screw extruder (length to diameter (L/D) ratio of 24 and length (L) of 0.381 m (15 inches)) with the temperature set at 249° C. (480° F.), 257° C. (495° F.), and 254° C. (490° F.) in the feeding zone, melting zone, and pumping zone, respectively. The screw was operated at 42 revolutions per minute (rpm) with a pressure drop of 21 MPa to 26 MPa (3000 to 3700 psi). The PVP-PU-PVP copolymer prepared as described in Example 11 was extruded from an identical single screw extruder with the temperature set at 204° C. (400° F.), 210° C. (410° F.), and 210° C. (410° F.) in the feeding zone, melting zone, pumping zone, respectively. The feed rate of this extruder was adjusted to ensure the right coating thickness. The extrudates from the two extruders met together in a tubing co-extrusion die that was heated to 221–232° C. (430–450° F.) and connected the two extruders. The die setup was such that the PVP-PU-PVP layer created the inner layer of the lumen while the PELLETHANE polymer created the outer layer of the lumen of the tubing. The two materials contacted and welded for a time during running through the die on the order of 10 seconds. The thickness of PVP-PU-PVP inner layer and PELLETHANE outer layer was controlled to be about 25.4 micrometers ($\mu$m) (0.001 inch) and 102 $\mu$m (0.004 inch), respectively, and the inner diameter (ID) and outer diameter (OD) of the tubing were controlled to be about 1.83 millimeters (mm) (0.072 inch) and 2.08 mm (0.082 inch), respectively, by adjusting the feeding rates (rpm) of the two extruders and properly setting up the geometry of the die. As soon as the co-extruded tubing came out from the die, it was quench-cooled by passing through a water tank. Thus, a tubing with the PELLETHANE layer sleeving the PVP-PU-PVP layer was created.

Example 36

Preparation of Lubricious Coating by Reactive Lamination of Lubricious Poly(vinylpyrrolidone)-Poly(acrylic acid) Random Copolymer (VA) to PELLETHANE 75D (PL75D) Film An alternative procedure to ensure the lubricious materials adhere strongly to the substrate involves reactive processing. To do this it is preferred to select lubricious polymers that can chemically react with the substrate. A copolymer composed of both the lubricious molecules and substrate molecules will form in situ during processing. This copolymer will firmly stay at the interface between the lubricious coating and the substrate because it automatically entangles with the both sides. In this example, the reactive lubricious material was a poly(vinylpyrrolidone)-poly(acrylic acid) copolymer, 96 kg/mol, obtained from Aldrich Chemical Co. In order to reduce the processing temperature, a low molecular weight (10 kg/mol) PVP, obtained from Aldrich Chemical Co., was mixed with the copolymer in a weight ratio of 10:90 by blending the dry powders. The carboxylic acid group of the copolymer is thought to couple with the urethane or hydroxyl groups of PELLETHANE, resulting in the formation of a graft copolymer. Films of the mixture and PELLETHANE PL75D, obtained from Dow Chemical Co., were prepared at 230° C. (446° F.) for 5 to 10 minutes with a hot press. The two films were laminated together at 230° C. (446° F.) for 5 to 10 minutes. The poly(vinylpyrrolidone)-poly(acrylic acid) side of the laminate was lubricious when it was wet, which lasted for two weeks.

Example 37

Preparation of Reactive-Coextruded Tubing with a Poly(vinyl pyrrolidone)-Poly(acrylic acid) Random Copolymer Lubricious Coating on the Surface of the Inner Lumen The lubricious poly(vinylpyrrolidone)-poly(acrylic acid) copolymer (mixed with a low molecular weight (10 kg/mol) PVP in a weight ratio of 10:90 as described in Example 36) was coextruded with PELLETHANE into tubing form. The PELLETHANE pellets were extruded with a single screw extruder as described in Example 35. The polymer mixture, prepared as described in Example 36, was extruded from an identical single screw extruder with the temperature set at 204° C. (400° F.), 207° C. (405° F.) and 216° C. (420° F.) in the feeding zone, melting zone, pumping zone, respectively. The feed rate of this extruder was adjusted to ensure the right coating thickness. The extrudates from the two extruders met together in a tubing co-extrusion die that was heated to 221–232° C. (430–450° F.) and connected the two extruders. The die setup was such that the poly(vinylpyrrolidone)-poly(acrylic acid) layer created the inner layer of the lumen while the PELLETHANE polymer created the outer layer of the lumen of the tubing. The two materials contacted and welded for a time during running through the die on the order of 10 seconds. The thickness of the poly(vinylpyrrolidone)-poly(acrylic acid) inner layer and PELLETHANE outer layer was controlled to be about 25.4 µm and 102 µm, respectively, and the ID and OD of the tubing were controlled to be about 1.83 mm and 2.08 mm, respectively, by adjusting the feeding rates (revolutions per minute, rpm) of the two extruders and properly setting up the geometry of the die. As soon as the co-extruded tubing came out from the die, it was quench-cooled by passing through a water tank. Thus, a tubing with the PELLETHANE layer sleeving the poly(vinylpyrrolidone)-poly(acrylic acid) layer was created.

Example 38

Lubricity Test of the Coextruded Tubing

An Imass Slip/Peel Tester Model SP-2000 was used to obtain quantitative data regarding the lubricity of the inner lumen of PELLETHANE tubing coextruded with the PVP-PU-PVP BLOCK copolymer of Example 11.

The ASTM method D-1894 was used as a guide for the determination of the coefficient of friction. An experiment was set up to pull a small diameter PELLETHANE tube through the inner lumen of the coextruded tubing of Example 35. A piece of tape was used to hold the coextruded tubing stationary and to provide resistance by keeping the tubing flat. The smaller diameter PELLETHANE tube was connected to the slip tester, and was pulled 31 mm (1.22 inch) through the coextruded tubing for each run. The tubing was kept wet with deionized water throughout the duration of the sled test. The instrument was set with the following parameters: 5 kg cell, 200 g sled, 2 second delay, 31 mm (1.22 inch) distance, 10 seconds averaging, 152 mm/minute (6 inch/minute) speed. Four sled test runs were performed on the coextruded tubing. The results of the runs were averaged and are reported in the table below. The same experiment was attempted on a sample of PELLETHANE tubing that was extruded before the copolymer was added to the extruder. The uncoated tubing did not allow the smaller diameter PELLETHANE tube to slide at all. Instead, the smaller PELLETHANE tube stretched as it was pulled, and COF measurements could not be made.

The static peak is defined as the maximum COF that occurs during the delay time. The kinetic peak is the maximum COF that occurs during the averaging time, while the valley reports the lowest COF measured during the averaging time. The reported average is an average of the COF measured during the ten second averaging time, and the root mean squared (RMS) shows the deviation from the average value.

|  | Coextruded Tubing |
| --- | --- |
| Static Peak | 0.581 |
| Kinetic Peak | 0.750 |
| Valley | 0.533 |
| Average | 0.671 |
| RMS | 0.050 |

This data indicates that the coextrusion of the PELLETHANE with the PVP-PU-PVP block copolymer substantially reduced the COF of the inner lumen, compared to regular PELLETHANE tubing.

The complete disclosure of all patents, patent documents, and publications cited herein are incorporated by reference, as if individually incorporated. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A medical device comprising a surface comprising a thermoplastic $A_nB$ block copolymer, wherein the A block comprises poly(vinyl pyrrolidone) units and the B block is a long-chain organic polymeric connecting unit comprising urethane groups, urea groups, imide groups, amide groups, ester groups, ether groups, or combinations thereof, wherein n is at least two, and further wherein the long-chain organic connecting unit comprises 20 atoms or more.

2. The medical device of claim 1 wherein the $A_nB$ block is an A-B-A block copolymer.

3. The medical device of claim 2 wherein the B block is a long-chain connecting unit comprising urethane groups, urea groups, or combinations thereof.

4. The medical device of claim 3 wherein the B block is a long-chain connecting unit comprising urethane groups.

5. The medical device of claim 2 wherein the A blocks comprise a copolymer of N-vinyl pyrrolidone and monomers nonreactive with isocyanate groups.

6. The medical device of claim 5 wherein the monomers nonreactive with isocyanate groups are selected from the group consisting of (meth)acrylic esters, (meth)acrylamides, butadiene, ethylene, alpha-olefins, halogenated olefins, acrylonitrile, isoprene, styrene, vinyl chloride, vinyl fluoride, vinyl esters, vinylidene chloride, N-vinyl carbazole, and combinations thereof.

7. The medical device of claim 2 wherein the A blocks are formed from a poly(vinyl pyrrolidone) having a weight average molecular weight of at least about 1000 g/mol.

8. The medical device of claim 7 wherein the A blocks are formed from a poly(vinyl pyrrolidone) having a weight average molecular weight of no greater than about $1\times10^6$ g/mol.

9. The medical device of claim 8 wherein the A blocks are formed from a poly(vinyl pyrrolidone) having a weight average molecular weight of no greater than about 400,000 g/mol.

10. The medical device of claim 2 wherein the A blocks are formed from substantially monofunctional hydroxyl terminated poly(vinyl pyrrolidone).

11. The medical device of claim 2 wherein the B block has about 100 atoms or more in the chain.

12. The medical device of claim 2 wherein the B block has no greater than about $1\times10^6$ atoms in the chain.

13. The medical device of claim 2 wherein the B block is formed from a diisocyanate terminated prepolymer.

14. The medical device of claim 2 wherein the B block further comprises tertiary amine groups, siloxane groups, silane groups, ortho-ester groups, phosphoester groups, thioether groups, sulfoxide groups, sulfone groups, ketone groups, acetal groups, ketal groups, hemiacetal groups, hemiketal groups, epoxy groups, or combinations thereof.

15. The medical device of claim 2 wherein the block copolymer has a weight average molecular weight of no greater than about $3\times10^6$ g/mol in the uncrosslinked state.

16. The medical device of claim 2 wherein the block copolymer is crosslinked.

17. The medical device of claim 2 wherein the block copolymer is in the form of a coating on a substrate.

18. The medical device of claim 17 wherein the coating is coextruded with the substrate.

19. The medical device of claim 2 which is in the form of a catheter.

20. The medical device of claim 19 wherein the catheter is in the form of a lead delivery catheter.

21. The medical device of claim 2 wherein the block copolymer is lubricious.

22. The medical device of claim 21 wherein a substrate coated with the block copolymer has a coefficient of friction at least 50% less than that of the uncoated substrate.

23. The medical device of claim 2 wherein the block copolymer is biocompatible.

24. The medical device of claim 2 wherein the surface comprises a mixture of a thermoplastic A-B-A block copolymer and a secondary polymer.

25. The medical device of claim 24 wherein the secondary polymer is a poly(vinyl pyrrolidone), a polyurethane, a polyurea, a poly(urethane-urea), a polyamide, a poly(amide-ether), a polyimide, copolymers or mixtures thereof.

26. A method of modifying a surface of a medical device, the method comprising:
preparing a thermoplastic $A_nB$ block copolymer, wherein the A block comprises poly(vinyl pyrrolidone) units and the B block is a long-chain organic polymeric connecting unit comprising urethane groups, urea groups, imide groups, amide groups, ether groups, ester groups, or combinations thereof, wherein n is at least two, and further wherein the long-chain organic connecting unit comprises 20 atoms or more; and
applying the $A_nB$ copolymer to the surface of the medical device.

27. The method of claim 26 wherein the $A_nB$ block copolymer is an A-B-A block copolymer.

28. The method of claim 27 wherein the B block is a long-chain connecting unit comprising urethane groups, urea groups, or combinations thereof.

29. The method of claim 27 wherein the B block is a long-chain connecting unit comprising urethane groups.

30. The method of claim 27 wherein the A blocks comprise a copolymer of N-vinyl pyrrolidone and monomers nonreactive with isocyanate groups.

31. The method of claim 30 wherein the monomers nonreactive with isocyanate groups are selected from the group consisting of (meth)acrylic esters, (meth)acrylamides, butadiene, ethylene, alpha-olefins, halogenated olefins, acrylonitrile, isoprene, styrene, vinyl chloride, vinyl fluoride, vinyl esters, vinylidene chloride, N-vinyl carbazole, and combinations thereof.

32. The method of claim 27 wherein the A blocks are formed from a poly(vinyl pyrrolidone) having a weight average molecular weight of at least about 1000 g/mol.

33. The method of claim 27 wherein the A blocks are formed from a poly(vinyl pyrrolidone) having a weight average molecular weight of no greater than about $1\times10^6$ g/mol.

34. The method of claim 27 wherein the A blocks are formed from substantially monofunctional hydroxyl terminated poly(vinyl pyrrolidone).

35. The method of claim 27 wherein the B block has about 100 atoms or more in the chain.

36. The method of claim 27 wherein the B block has no greater than about $1\times10^6$ atoms in the chain.

37. The method of claim 27 wherein the B block is formed from a diisocyanate terminated prepolymer.

38. The method of claim 27 wherein the B block further comprises tertiary amine groups, siloxane groups, silane groups, ortho-ester groups, phosphoester groups, thioether groups, sulfoxide groups, sulfone groups, ketone groups, acetal groups, ketal groups, hemiacetal groups, hemiketal groups, epoxy groups, or combinations thereof.

39. The method of claim 27 wherein the block copolymer has a weight average molecular weight of no greater than about $3\times10^6$ g/mol in the uncrosslinked state.

40. The method of claim 27 wherein the block copolymer is crosslinked.

41. The method of claim 27 wherein applying the block copolymer to the surface of the medical device comprises applying the block copolymer out of a solution.

42. The method of claim 41 wherein applying the block copolymer to the surface of the medical device out of solution comprises applying the block copolymer by dip coating, roll coating, spraying, inkjet printing, or combinations thereof.

43. The method of claim 27 wherein applying the block copolymer to the surface of the medical device comprises coextruding the block copolymer with a substrate polymer.

44. The method of claim 43 wherein coextruding comprises reactively coextruding the block copolymer.

45. The method of claim 27 wherein applying the block copolymer to the surface of the medical device comprises applying a mixture of the block copolymer with a secondary polymer.

46. The method of claim 45 wherein the secondary polymer is a poly(vinyl pyrrolidone), a polyurethane, a polyurea, a poly(urethane-urea), a polyamide, a poly(amide-ether), a polyimide, copolymers or mixtures thereof.

47. A thermoplastic $A_nB$ block copolymer, wherein the A blocks comprise poly(vinyl pyrrolidone) units and the B block is a long-chain organic polymeric connecting unit comprising urethane groups, urea groups, imide groups, amide groups, ether groups, or combinations thereof, wherein n is at least two, and further wherein the long-chain organic connecting unit comprises 20 atoms or more.

48. The block copolymer of claim 47 wherein the $A_nB$ block copolymer is an A-B-A block copolymer.

49. The block copolymer of claim 48 wherein the B block is a long-chain connecting unit comprising urethane groups, urea groups, or combinations thereof.

50. The block copolymer of claim 48 wherein the B block is a long-chain connecting unit comprising urethane groups.

51. The block copolymer of claim 48 wherein the A blocks comprise a copolymer of N-vinyl pyrrolidone and monomers nonreactive with isocyanate groups.

52. The block copolymer of claim 48 wherein the A blocks are formed from a poly(vinyl pyrrolidone) having a weight average molecular weight of at least about 1000 g/mol.

53. The block copolymer of claim 48 wherein the A blocks are formed from a poly(vinyl pyrrolidone) having a weight average molecular weight of no greater than about $1\times10^6$ g/mol.

54. The block copolymer of claim 48 wherein the A blocks are formed from substantially monofunctional hydroxyl terminated poly(vinyl pyrrolidone).

55. The block copolymer of claim 48 wherein the B block has about 100 atoms or more in the chain.

56. The block copolymer of claim 48 wherein the B block has no greater than about $1\times10^6$ atoms in the chain.

57. The block copolymer of claim 48 wherein the B block is formed from a diisocyanate terminated prepolymer.

58. The block copolymer of claim 48 wherein the B block further comprises tertiary amine groups, siloxane groups, silane groups, ortho-ester groups, phosphoester groups, thio-ether groups, sulfoxide groups, sulfone groups, ketone groups, acetal groups, ketal groups, hemiacetal groups, hemiketal groups, epoxy groups, or combinations thereof.

59. The block copolymer of claim 48 wherein the block copolymer has a weight average molecular weight of no greater than about $3\times10^6$ g/mol in the uncrosslinked state.

60. The block copolymer of claim 48 wherein the block copolymer is crosslinked.

61. The block copolymer of claim 48 wherein the block copolymer is in the form of a coating on a substrate.

62. A method of preparing a thermoplastic $A_nB$ block copolymer, the method comprising reacting a substantially monofunctional poly(vinyl pyrrolidone) with a functionalized B-block precursor comprising functional groups reactive with the functional groups of the poly(vinyl pyrrolidone) to form the thermoplastic $A_nB$ block copolymer, wherein the A blocks comprise poly(vinyl pyrrolidone) units and the B block is a long-chain organic polymeric connecting unit comprising urethane groups, urea groups, imide groups, amide groups, ether groups, or combinations thereof, wherein n is at least two, and further wherein the long-chain organic connecting unit comprises 20 atoms or more.

63. The method of claim 62 wherein the $A_nB$ block copolymer is an A-B-A block copolymer.

64. The method of claim 62 wherein the substantially monofunctional poly(vinyl pyrrolidone) is hydroxyl terminated.

65. The method of claim 64 wherein the monofunctional hydroxyl terminated poly(vinyl pyrrolidone) is prepared by polymerizing N-vinyl pyrrolidone in the presence of a hydroxyl terminated chain transfer agent.

66. The method of claim 62 wherein the hydroxyl terminated chain transfer agent is isopropoxyethanol.

67. The method of claim 62 wherein the functionalized B-block precursor is a diisocyanate terminated prepolymer comprising urethane groups, urea groups, amide groups, imide groups, ether groups, or combinations thereof.

68. The method of claim 67 wherein the functionalized B-block precursor is a diisocyanate terminated prepolymer comprising urethane groups, urea groups, or combinations thereof.

69. The method of claim 62 wherein the reacting step comprises reactively coextruding the substantially monofunctional poly(vinyl pyrrolidone) with the functionalized B-block precursor.

70. A method of preparing a thermoplastic $A_nB$ block copolymer, the method comprising reacting a substantially monofunctional poly(vinyl pyrrolidone) with functionalized B-block precursor reactants to form the thermoplastic $A_nB$ block copolymer, wherein the A blocks comprise poly(vinyl pyrrolidone) units and the B block is a long-chain organic polymeric connecting unit comprising urethane groups, urea groups, imide groups, amide groups, ether groups, or combinations thereof, wherein n is at least two, and further wherein the long-chain organic connecting unit comprises 20 atoms or more.

* * * * *

UNITED STATES PATENT AND TRADEMARK OFFICE
CERTIFICATE OF CORRECTION

| | | |
|---|---|---|
| PATENT NO. | : 6,756,449 B2 | Page 1 of 1 |
| APPLICATION NO. | : 10/246806 | |
| DATED | : June 29, 2004 | |
| INVENTOR(S) | : Michael Eric Benz, SuPing Lyu and Julie Ann Alkatoutt | |

It is certified that error appears in the above-identified patent and that said Letters Patent is hereby corrected as shown below:

On the title page, item [54] & column 1, line 1, should read:
-- Title: $A_nB$ Block Copolymers Containing Poly (Vinyl Pyrrolidone) Units, Medical Devices and Methods --.

Signed and Sealed this

Fifth Day of February, 2008

JON W. DUDAS
*Director of the United States Patent and Trademark Office*